(12) United States Patent
Schulte et al.

(10) Patent No.: US 8,754,194 B2
(45) Date of Patent: Jun. 17, 2014

(54) MODIFIED COAGULATION FACTORS WITH PROLONGED IN VIVO HALF-LIFE

(75) Inventors: Stefan Schulte, Marburg (DE); Thomas Weimer, Gladenbach (DE); Hubert Metzner, Marburg (DE)

(73) Assignee: CSL Behring GmbH, Marburg (DE)

( * ) Notice: Subject to any disclaimer, the term of this patent is extended or adjusted under 35 U.S.C. 154(b) by 605 days.

(21) Appl. No.: 12/520,840

(22) PCT Filed: Dec. 21, 2007

(86) PCT No.: PCT/EP2007/011356
§ 371 (c)(1),
(2), (4) Date: Jul. 23, 2009

(87) PCT Pub. No.: WO2008/077616
PCT Pub. Date: Jul. 3, 2008

(65) Prior Publication Data
US 2010/0120664 A1    May 13, 2010

Related U.S. Application Data

(60) Provisional application No. 60/879,334, filed on Jan. 9, 2007.

(30) Foreign Application Priority Data

Dec. 22, 2006   (EP) ..................... 06026747

(51) Int. Cl.
A61K 38/37   (2006.01)
C07K 1/00    (2006.01)

(52) U.S. Cl.
USPC .......... 530/381; 530/362; 514/14.1; 514/15.2

(58) Field of Classification Search
CPC ......... A61K 38/37; C07K 14/76; C07K 16/00
See application file for complete search history.

(56) References Cited

U.S. PATENT DOCUMENTS

| | | | |
|---|---|---|---|
| 4,784,950 A | 11/1988 | Hagen et al. | |
| 4,970,300 A | 11/1990 | Fulton et al. | |
| 5,364,771 A | 11/1994 | Lollar et al. | |
| 5,876,969 A * | 3/1999 | Fleer et al. | 435/69.7 |
| 6,177,059 B1 * | 1/2001 | Matsuda et al. | 424/1.21 |
| 6,403,077 B1 | 6/2002 | Strom et al. | |
| 6,548,653 B1 | 4/2003 | Young et al. | |
| 7,122,634 B2 * | 10/2006 | Lollar | 530/383 |
| 7,404,956 B2 | 7/2008 | Peters et al. | |
| 7,939,632 B2 | 5/2011 | Metzner et al. | |
| 2003/0199043 A1 | 10/2003 | Ballance et al. | |
| 2004/0087778 A1 * | 5/2004 | Feige et al. | 530/391.1 |
| 2005/0266533 A1 | 12/2005 | Ballance et al. | |
| 2009/0042787 A1 | 2/2009 | Metzner et al. | |
| 2009/0298760 A1 | 12/2009 | Weimer et al. | |
| 2010/0222554 A1 | 9/2010 | Weimer et al. | |
| 2011/0189182 A1 | 8/2011 | Metzner et al. | |

FOREIGN PATENT DOCUMENTS

| | | |
|---|---|---|
| EP | 0 770 625 B1 | 7/2002 |
| EP | 1 444 986 A1 | 8/2004 |
| EP | 1 816 201 A1 | 8/2007 |
| EP | 1 867 660 A1 | 12/2007 |
| WO | WO 91/09125 A1 | 6/1991 |
| WO | WO 94/15625 A1 | 7/1994 |
| WO | WO 96/01653 A1 | 1/1996 |
| WO | WO 97/03193 A1 | 1/1997 |
| WO | WO 97/11957 A1 | 4/1997 |
| WO | WO 97/40145 A1 | 10/1997 |
| WO | WO 99/55306 A1 | 11/1999 |
| WO | WO 00/71714 A2 | 11/2000 |
| WO | WO 01/01749 A2 | 1/2001 |
| WO | WO 01/58935 A2 | 8/2001 |
| WO | WO 01/58957 A2 | 8/2001 |
| WO | WO 01/68109 A1 | 9/2001 |
| WO | WO 01/79271 A1 | 10/2001 |
| WO | WO 02/04598 A2 | 1/2002 |
| WO | WO 02/04598 A3 | 1/2002 |
| WO | WO 02/29025 A3 | 4/2002 |
| WO | WO 02/32461 A2 | 4/2002 |
| WO | WO 02/060951 A2 | 8/2002 |
| WO | WO 02/072023 A2 | 9/2002 |
| WO | WO 02/103024 A2 | 12/2002 |
| WO | WO 03/059935 A2 | 7/2003 |
| WO | WO 03/059935 A3 | 7/2003 |
| WO | WO 03/068934 A2 | 8/2003 |
| WO | WO 03/068934 A3 | 8/2003 |
| WO | WO 03/076557 A2 | 9/2003 |
| WO | WO 03/087355 A1 | 10/2003 |

(Continued)

OTHER PUBLICATIONS

International Search Report and Written Opinion, mailed Mar. 26, 2008, in International Patent Application No. PCT/EP2007/011356.

(Continued)

*Primary Examiner* — Christina Bradley
*Assistant Examiner* — Jeanette Lieb
(74) *Attorney, Agent, or Firm* — Finnegan, Henderson, Farabow, Garrett & Dunner, LLP

(57) ABSTRACT

The present invention relates to nucleic acid sequences coding for modified coagulation factors, preferably coagulation factor VIII, and their derivatives; recombinant expression vectors containing such nucleic acid sequences; host cells transformed with such recombinant expression vectors; and recombinant polypeptides and derivatives coded for by said nucleic acid sequences, whereby said recombinant polypeptides and derivatives have biological activities and prolonged in vivo half-lives compared to the unmodified wild-type proteins. The invention also relates to corresponding sequences that result in improved in vitro stability. The present invention further relates to processes for the manufacture of such recombinant proteins and their derivatives. The invention also relates to a transfer vector for use in human gene therapy, which comprises such nucleic acid sequences.

15 Claims, 6 Drawing Sheets

(56) References Cited

FOREIGN PATENT DOCUMENTS

| WO | WO 03/093313 A2 | 11/2003 | | |
|----|----|----|----|----|
| WO | WO 2004/005347 A1 | 1/2004 | | |
| WO | WO 2004/021861 A2 | 3/2004 | | |
| WO | WO 2004/021861 A3 | 3/2004 | | |
| WO | WO 2004/081053 A1 | 9/2004 | | |
| WO | WO 2004/082640 A2 | 9/2004 | | |
| WO | WO 2004/101739 A2 | 11/2004 | | |
| WO | WO 2004/101739 A3 | 11/2004 | | |
| WO | WO 2004/101740 A2 | 11/2004 | | |
| WO | WO 2005/000892 A2 | 1/2005 | | |
| WO | WO 2005/001025 A2 | 1/2005 | | |
| WO | WO 2005/024044 A2 | 3/2005 | | |
| WO | WO 2006/027111 A1 | 3/2005 | | |
| WO | WO 2005/063808 A1 | 7/2005 | | |
| WO | WO 2005/111074 A1 | 11/2005 | | |
| WO | WO 2005/111225 A1 | 11/2005 | | |
| WO | WO 2006/000448 A2 | 1/2006 | | |
| WO | WO 2006/018204 A1 | 2/2006 | | |
| WO | WO 2006/108590 A1 | 10/2006 | | |
| WO | WO2006/108590 A1 * | 10/2006 | ........... | C07K 14/755 |
| WO | WO 2006108590 A1 * | 10/2006 | | |
| WO | WO 2007/115724 A2 | 10/2007 | | |
| WO | WO 2008/098720 A1 | 8/2008 | | |

OTHER PUBLICATIONS

European Search Report, mailed May 9, 2007, in European Patent Application No. EP 06 02 6747.
Aledort, "Comparative thrombotic event incidence after infusion of recombinant factor VIIa versus factor VIII inhibitor bypass activity" Journal of Thrombosis and Haemostasis, 2004, vol. 2, pp. 1700-1708.
Amano et al., "Mutation at either Arg336 or Arg562 in Factor VIII Is Insufficient for Complete Resistance to Activated Protein C (APC)-mediated Inactivation: Implications for the APC Resistance Test" Thrombosis and Haemostasis, 1998, vol. 79, pp. 557-563.
Ananyeva et al., "Catabolism of the Coagulation Factor VIII" TCM, 2001, vol. 11, No. 6, pp. 251-257.
Ausubel et al., Current Protocols in Molecular Biology, Supplement 58, John Wiley & Sons, Inc., 1987, Table of Contents.
Beattie et al., "Structure and evolution of human α-fetoprotein deduced from partial sequence of cloned cDNA" Gene, 1982, vol. 20, pp. 415-422.
Bick et al., "Factor V: a Simplified One-Stage Assay using a Stabilized Artificial Substrate" Beitrage Zur Pathologie BD, 1973, vol. 150, pp. 311-315.
Chavin et al., "Blood Clotting Factor IX" The Journal of Biological Chemistry, Mar. 25, 1984, vol. 259, No. 6, pp. 3387-3390.
Collins et al., "Molecular cloning of the human gene for von Willebrand factor and identification of the transcription initiation site" Proceedings of the National Academy of Sciences, USA, Jul. 1987, vol. 84, pp. 4393-4397.
Comp et al., "Determination of Functional Levels of Protein C, an Antithrombotic Protein, Using Thrombin-Thrombomodulin Complex" Blood, Jan. 1984, vol. 63, No. 1, pp. 15-21.
Cooke et al., "Serum Vitamin D-binding Protein is a Third Member of the Albumin and Alpha Fetoprotein Gene Family" Journal of Clinical Investigation, Dec. 1985, vol. 76, pp. 2420-2424.
Dumont et al., "Monomeric Fc Fusions" Blodrugs, 2006, vol. 20, No. 3, pp. 151-160.
Fay et al., "Human Factor VIIIa Subunit Structure" The Journal of Biological Chemistry, May 15, 1991, vol. 266, No. 14, pp. 8957-8962.
Fay et al., "Characterization of the Interaction between the A2 Subunit and A1/A3-C1-C2 Dimer in Human Factor VIIIa" The Journal of Biological Chemistry, Jul. 5, 1992, vol. 267, No. 19, pp. 13246-13250.
Federici et al., "A sensitive ristocetin co-factor activity assay with recombinant glycoprotein Ibo for the diagnosis of patients with low von Willebrand factor levels," Haematologica, Jan. 2004, vol. 89, No. 1, pp. 77-85.
Frokjaer et al., "Pharmaceutical Formulation Development of Peptides and Proteins" European Journal of Pharmaceutics and Biopharmaceutics, 2000, vol. 50, p. 329.
Gale et al., "Interdomain engineered disulfide bond permitting elucidation of mechanisms of inactivation of coagulation factor Va by activated protein C" Protein Science, 2002, vol. 11, pp. 2091-2101.
Gale et al., "An engineered interdomain disulfide bond stabilizes human blood coagulation factor VIIIa" Journal of Thrombosis and Haemostasis, 2003, vol. 1, pp. 1966-1971.
Gale et al., "Intrinsic stability and functional properties of disulfide bond-stabilized coagulation factor VIIIa variants" Journal of Thrombosis and Haemostasis, 2006, vol. 4, pp. 1315-1322.
Heeb et al., "Protein S multimers and monomers each have direct anticoagulant activity" Journal of Thrombosis and Haemostasis, 2006, vol. 4, pp. 385-391.
Kallas et al., "The von Willebrand factor collagen-binding activity assay: clinical application" Annals of Hematology, 2001, vol. 80, pp. 466-471.
Lichenstein et al., "Afamin Is a New Member of the Albumin, α-fetoprotein, and Vitamin D-binding Protein Gene Family" The Journal of Biological Chemistry, Jul. 8, 1994, vol. 269, No. 27, pp. 18149-18154.
Lin et al., "Use of blood outgrowth endothelial cells for gene therapy for hemophilia A" Blood, Jan. 15, 2002, vol. 99, No. 2, pp. 457-462.
Lollar, "Characterization of Factor VIII B-Cell Inhibitory Epitopes" Thrombosis and Haemostasis, 1999, vol. 82, No. 2, pp. 505-508.
Miao et al., "Bioengineering of coagulation factor VIII for improved secretion" Blood, May 1, 2004, vol. 103, No. 9, pp. 3412-3419.
Morrissey et al., "Quantitation of Activated Factor VII Levels in Plasma Using a Tissue Factor Mutant Selectively Deficient in Promoting Factor VIII Activation" Blood, Feb. 1, 1993, vol. 81, No. 3, pp. 734-744.
Nakayama, "Furin: a mammalian subtilisin/Kex2p-like endoprotease involved in processing of a wide variety of precursor proteins" Biochemistry Journal, 1997, vol. 327, pp. 625-635.
Oh et al., "Synthesis of recombinant blood coagulation factor VIII (FVIII) heavy and light chains and reconstitution of active form of FVIII" Experimental and Molecular Medicine, Jun. 1999, vol. 31, No. 2, pp. 95-100.
Petrovan et al., "A Novel Clotting Assay for Quantitation of Plasma Prothrombin (Factor II) Using *Echis multisquamatus* Venom" American Journal of Clinical Pathology, 1999, vol. 112, pp. 705-711.
Pipe et al., "Characterization of a genetically engineered inactivation-resistant coagulation factor VIIIa" Proceedings of the National Academy of Sciences USA, Oct. 1997, vol. 94, pp. 11851-11856.
Pipe, "Coagulation Factors with Improved Properties for Hemophilia Gene Therapy" Seminars in Thrombosis and Hemostasis, 2004, vol. 30, No. 2, pp. 227-237.
Pittman et al., "Biochemical Immunological and In Vivo Functional Characterization of B-Domain-Deleted Factor VIII" Blood, Jun. 1, 1993, vol. 81, No. 11, pp. 2925-2935.
Rizza et al., "Coagulation Assay of VIIIC and IXC" In: The Hemophilias, New York Churchchill Livingstone, Bloom (ed.), 1982, Chapter 2, pp. 18-38.
Rosén, "Assay of Factor VIII:C with a Chromogenic Substrate" Scandinavian Journal of Haematology Supplement 40, 1984, vol. 33, pp. 139-145.
Saenko et al., "Molecular defects in coagulation Factor VIII and their impact on Factor VIII function" Vox Sanguinis, vol. 83, pp. 89-96.
Seligsohn et al., "Coupled Amidolytic Assay for Factor VII: Its Use With a Clotting Assay to Determine the Activity State of Factor VII" Blood, Nov. 1978, vol. 52, No. 5, pp. 978-988.
Sheffield et al.: "Effects of genetic fusion of factor IX to albumin on in vivo clearance in mice and rabbits" British Journal of Haematology, Oxford, GB, 2004, vol. 126, pp. 565-573.
Sucker et al., "Determination of von Willebrand Factor Activity: Evaluation of the HaemosIL™ Assay in Comparison With Established Procedures" Clinical and Applied Thrombosis/Hemostasis, Jul. 2006, vol. 12, No. 3, pp. 305-310.
Swaroop et al., "Mutagenesis of a Potential Immunoglobulin-binding Protein-binding Site Enhances Secretion of Coagulation Factor VIII" The Journal of Biological Chemistry, Sep. 26, 1997, vol. 272, No. 39, pp. 24121-24124.

(56) References Cited

OTHER PUBLICATIONS

Tabatabai et al., "Protein Z Circulates in Plasma in a Complex with Protein Z-Dependent Protease Inhibitor" Thrombosis and Haemostasis, 2001, vol. 85, pp. 655-660.
Van Wijk et al., "A Rapid Manual Chromogenic Factor X Assay" Thrombosis Research, 1981, vol. 22, pp. 681-686.
Vehar et al,; "Structure of human factor VIII" Nature, Nov. 22, 1984, vol. 312, pp. 337-342.
Wakabayashi et al., "A Glu113Ala Mutation within a Factor VIII $Ca^{2+}$-Binding Site Enhances Cofactor Interactions in Factor Xase" Biochemistry, 2005, vol. 44, pp. 10298-10304.
Wood et al., "Expression of active human factor VIII from recombinant DNA clones" Nature, Nov. 22, 1984, vol. 312, pp. 330-337.
Berrettini et al., "Pharmacokinetic Evaluation of Recombinant, Activated Factor VII in Patients with Inherited Factor VII Deficiency" *Haematologica*, 86(6):640-645 (2001).
Bick, R.L. et al., "Physiology of Hemostasis" *Clin. Lab. Med.*, 14(4):677-707 (1994).
Brinkhous et al., "Effect of Recombinant Factor VIIa on the Hemostatic Defect in Dogs with Hemophilia A, Hemophilia B, and von Willebrand Disease" *Proc. Natl. Acad. Sci. USA*, 86:1382-1386 (1989).
Chaudhury, C. et al., "The Major Histocompatibility Complex-related Fc Receptor for IgG (FcRn) Binds Albumin and Prolongs Its Lifespan" *J. Exp. Med.*, 197(3):315-322 (2003).
Colman, R.W. et al. (eds.), in *Homeostasis and Thrombosis: Basic Principles & Clinical Practice*. 4th ed., Philadelphia, Lippincott Williams & Wilkins, 2001; pp. 34-35, 40-41, 103-104, 128-129, 159, 176, and 194.
Colman, R.W. et al. (eds.), in *Homeostasis and Thrombosis: Basic Principles & Clinical Practice*. 4th ed., Philadelphia, Lippincott Williams & Wilkins, 2001; Chapter 1, pp. 1-16.
Di Scipio, R.G. et al., "A Comparison of Human Prothrombin, Factor IX (Christmas Factor), Factor X (Stuart Factor), and Protein S" *Biochemistry*, 16(4):698-706 (1977).
Doolittle, R.F., "The Evolution of Vertebrate Blood Coagulation: A Case of Yin and Yang" *Thromb. Haemost.*, 70:24-28 (1993).
Duttaroy, A. et al., "Development of a Long-Acting Insulin Analog Using Albumin Fusion Technology" *Diabetes*, 54:251-258 (2005).
Erhardtsen, "To General Haemostasis—The Evidence-Based Route" *Pathophysiology of Haemostasis and Thrombosis*, 32(suppl. 1):47-52 (2002).
European Search Report and Opinion issued in Application No. 06002359.5-2401, dated Aug. 22, 2006.
European Search Report and Opinion issued in Application No. 06012262.9-2403, dated Jan. 24, 2007.
European Search Report and Opinion issued in Application No. 10164043.1-1212, dated Aug. 24, 2010.
European Search Report and Opinion issued in Application No. 10168156.7-1212, dated Nov. 22, 2010.
European Search Report and Opinion issued in Application No. 10168453.8-2403, dated Oct. 7, 2010.
Ewenstein et al., "Pharmacokinetic Analysis of Plasma-Derived and Recombinant F IX Concentrates in Previously Treated Patients with Moderate or Severe Hemophilia B" *Transfusion*, 42:190-197 (2002).
Greenberg et al., "Blood Coagulation Factors: Their Complementary DNAs, Genes, and Expression" in *Homeostasis and Thrombosis: Basic Principles & Clinical Practice*. 4th ed., Philadelphia, Lippincott Williams & Wilkins, 2001; Chapter 3, pp. 21-57.
Halpern, W. et al., "Albugranin™, a Recombinant Human Granulocyte Colony Stimulating Factor (G-CSF) Genetically Fused to Recombinant Human Albumin Induces Prolonged Myelopoietic Effects in Mice and Monkeys" *Pharmaceutical Research*, 19(11):1720-1729 (2002).
Hansson, K. et al., "Post-Translational Modifications in Proteins Involved in Blood Coagulation" *J. Thromb. Haemost.*, 3:2633-2648 (2005).
Holt, L.J. et al., "Domain Antibodies: Proteins for Therapy" *Trends in Biotechnology*, 21(11):484-490 (2003).

International Search Report and Written Opinion issued in International Patent Application No. PCT/EP2007/000937; Date of Mailing: May 18, 2007.
International Search Report and Written Opinion issued in International Patent Application No. PCT/EP2007/002948; Date of Mailing: Jan. 24, 2008.
International Search Report and Written Opinion issued in International Patent Application No. PCT/EP2007/005246; Date of Mailing: Sep. 28, 2007.
Kurachi, K. et al., "Isolation and Characterization of a cDNA Coding for Human Factor IX" *Proc. Natl. Acad. Sci. USA*, 79:6461-6464 (1982).
Lindley et al. "Pharmacokinetics and Pharmacodynamics of Recombinant Factor VIIa" *Clinical Pharmacology & Therapeutics*, 55(6):638-648 (1994).
Lusher, J.M., et al., "In Vivo Recovery with Products of Very High Purity-Assay Discrepancies" *Haemophilia*, 4(4):641-645 (1998).
Marques, J.A. et al., "A Barbourin-Albumin Fusion Protein that Is Slowly Cleared In Vivo Retains the Ability to Inhibit Platelet Aggregation In Vitro" *Thromb. Haemost.*, 86:902-908 (2001).
Melder, R.J. et al., "Pharmacokinetics and in vitro and in vivo antitumor response of an interleukin-2-human serum albumin fusion protein in mice" *Cancer Immunol. Immunother.*, 54:535-547 (2005).
Mikaelsson, M. et al., "Potency and In Vivo Recovery of High Purity Factor VIII Concentrates" *Thromb. Haemost.*, 72(1):160-161 (1994).
Mollerup et al., "The Use of RP-HPLC for Measuring Activation and Cleavage of rFVIIa During Purification" *Biotechnology and Bioengineering*, 48:501-505 (1995).
O'Reilly, M.S. et al., "Antiangiogenic Activity of the Cleaved Conformation of the Serpin Antithrombin" *Science*, 285:1926-1928 (1999).
Osborn, B.L. et al., "Albutropin: A Growth Hormone-Albumin Fusion with Improved Pharmacokinetics and Pharmacodynamics in Rats and Monkeys" *Eur. J. Pharmacol.*, 456:149-158 (2002).
Osborn, B.L. et al., "Pharmacokinetic and Pharmacodynamic Studies of a Human Serum Albumin-Interferon-α Fusion Protein in Cynomolgus Monkeys" *J. Pharmacol. Exper. Ther.*, 303:540-548 (2002).
Persson, E., "Structure of Human Coagulation Activated Factor VII," *Blood Coagulation and Fibrinolysis*, 11(Suppl. 1):S15-S17 (2000).
Poon, M-C. et al., "Recombinant Factor IX Recovery and Inhibitor Safety: A Canadian Post-licensure Surveillance Study" *Throm. Haemost.* 87:431-435 (2002).
Prescott, M. et al., "The Length of Polypeptide Linker Affects the Stability of Green Fluorescent Protein Fusion Proteins" *Anal. Biochem.*, 273:305-307 (1999).
Schulte, S., "Use of albumin fusion technology to prolong the half-life of recombinant factor VIIa" *Thromb. Res.*, 122(Suppl. 4):S14-S19 (2008).
Shah, A.M. et al., "Manipulation of the Membrane Binding Site of Vitamin K-Dependent Proteins: Enhanced Biological Function of Human Factor VII" *Proc. Natl. Acad. Sci. U.S.A.*, 95:4229-4234 (1998).
Sheffield, W.P. et al., "Prolonged in vivo anticoagulant activity of a hirudin-albumin fusion protein secreted from *Pichia pastoris*" *Blood Coagulation and Fibrinolysis*, 12:433-443 (2001).
Sheffield, W.P., et al., "Effects of Genetic Fusion of Factor IX to Albumin on In Vivo Clearance in Mice and Rabbits" *Br. J. Haematol.*, 126(4):565-573 (2004).
Stenflo, J., "Contributions of Gla and EGF-Like Domains to the Function of Vitamin K-Dependent Coagulation Factors" *Critical Reviews™ in Eukaryotic Gene Expression*, 9:59-88 (1999).
Sung, C., et al., "An IFN-β-Albumin Fusion Protein That Displays Improved Pharmacokinetic and Pharmacodynamic Properties in Nonhuman Primates" *Journal of Interferon and Cytokine Research*, 23(1):25-36 (2003).
Syed, S. et al., "Potent Antithrombin Activity and Delayed Clearance from the Circulation Characterize Recombinant Hirudin Genetically Fused to Albumin" *Blood*, 89(9):3243-3252 (1997).
U.S. Appl. No. 11/812,016: Advisory Action, mailed Oct. 25, 2010.
U.S. Appl. No. 11/812,016: Final Office Action, mailed Jul. 20, 2010.
U.S. Appl. No. 11/812,016: Non-Final Office Action, mailed Dec. 7, 2009.

(56) References Cited

OTHER PUBLICATIONS

U.S. Appl. No. 11/812,016: Restriction Requirement, mailed Jul. 15, 2009.
U.S. Appl. No. 12/000,739: Non-Final Office Action, mailed Jul. 21, 2010.
U.S. Appl. No. 12/000,739: Notice of Allowance, mailed Dec. 30, 2010.
U.S. Appl. No. 12/000,739: Restriction Requirement, mailed Mar. 31, 2010.
U.S. Appl. No. 12/223,616: Final Office Action, mailed Jun. 9, 2011.
U.S. Appl. No. 12/223,616: Non-Final Office Action, mailed Sep. 1, 2010.
U.S. Appl. No. 12/223,616: Restriction Requirement, mailed May 24, 2010.
U.S. Appl. No. 12/226,188: Final Office Action, mailed Dec. 21, 2011.
U.S. Appl. No. 12/226,188: Non-Final Office Action, mailed May 12, 2011.
U.S. Appl. No. 12/520,840: Non-Final Office Action, mailed Dec. 7, 2011.
U.S. Appl. No. 12/520,840: Restriction Requirement, mailed Oct. 13, 2011.
U.S. Appl. No. 13/074,153: Non-Final Office Action, mailed Feb. 23, 2012.
Wang, W. et al., "AlbuBNP, a Recombinant B-Type Natriuretic Peptide and Human Serum Albumin Fusion Hormone, as a Long-Term Therapy of Congestive Heart Failure" *Pharmaceutical Research*, 21:2105-2111 (2004).
Wasley et al., "PACE/Furin Can Process the Vitamin K-Dependent Pro-Factor IX Precursor within the Secretory Pathway" *J. Biol. Chem.*, 268(12):8458-8465 (1993).
Weimer, T. et al., "Prolonged in-vivo half-life of factor VIIa by fusion to albumin" *Thromb. Haemost.*, 99:659-667 (2008).
White et al. "Clinical Evaluation of Recombinant Factor IX", *Seminars in Hematology*, 35(2 Suppl 2):33-38 (1998).
White et al., "Recombinant Factor IX" *Thrombosis and Haemostasis*, 78(1):261-265 (1997).
Wriggers, W. et al., "Control of Protein Functional Dynamics by Peptide Linkers" *Biopolymers (Peptide Science)*, 80:736-746 (2005).
Xue, F. et al., "LINKER: a web server to generate peptide sequences with extended conformation" *Nucl. Acids Res.*, 32:W562-W565 (2004).
Yao, Z. et al., "Effect of Albumin Fusion on the Biodistribution of Interleukin-2" *Cancer Immunol. Immunother.*, 53:404-410 (2004).
Yeh et al. "Design of yeast-secreted albumin derivatives for human therapy: biological and antiviral properties of a serum albunin-CD4 genetic conjugate", *Proc. Natl. Acad. Sci. USA*, 89(5):1904-1908 (1992).
Zollner, S. et al., "Prolonged serum half-life of a recombinant, albumin-fused, human coagulation factor I(rIX-FP) in different animal species" Poster from the 2010 Hemophilia World Congress sponsored by the World Federation of Hemophilia, in Buenos Aires, Argentina, Jul. 10-Jul. 14, 2010.
Office Action in Japanese Patent Application No. 2009-541911 dated Apr. 2, 2013, together with English Translation.
Pipe, S, W. "Functional Roles of the Factor VIII B Domain," *Haemophilia* 15: 1187-1196 (2009).
Pittman et al., "Biochemical, Immunological, and In Vivo Functional Characterization of B-Domain-Deleted Factor VIII," *Blood* 81(11): 2925-2935 (1993).
Japanese Office Action for Japanese Patent Application No. 2009-541911 dated Jul. 3, 2012.
Australian Office Action for Australian Patent Application No. 2007338298 dated Nov. 23, 2011.
Condensed Table of FVIII Point Mutations, as downloaded from http://hadb.org.uk/WebPages/PublicFiles/CondensedPoints.htm, Feb. 11, 2013.

* cited by examiner

Figure 1a: B domain sequence replacements in FVIII albumin insertion proteins used in the examples. The transition sequences shown for pF8-1210 correspond to SEQ ID NO. 24 (A2/B/Albumin) and 34 (Albumin/B/A3), for pF8-1211 to SEQ ID NO. 24 and 35, for pF8-1413 to SEQ ID NO. 23 and 35 and for pF8-1439 to SEQ ID NO: 28 and 40, respectively.

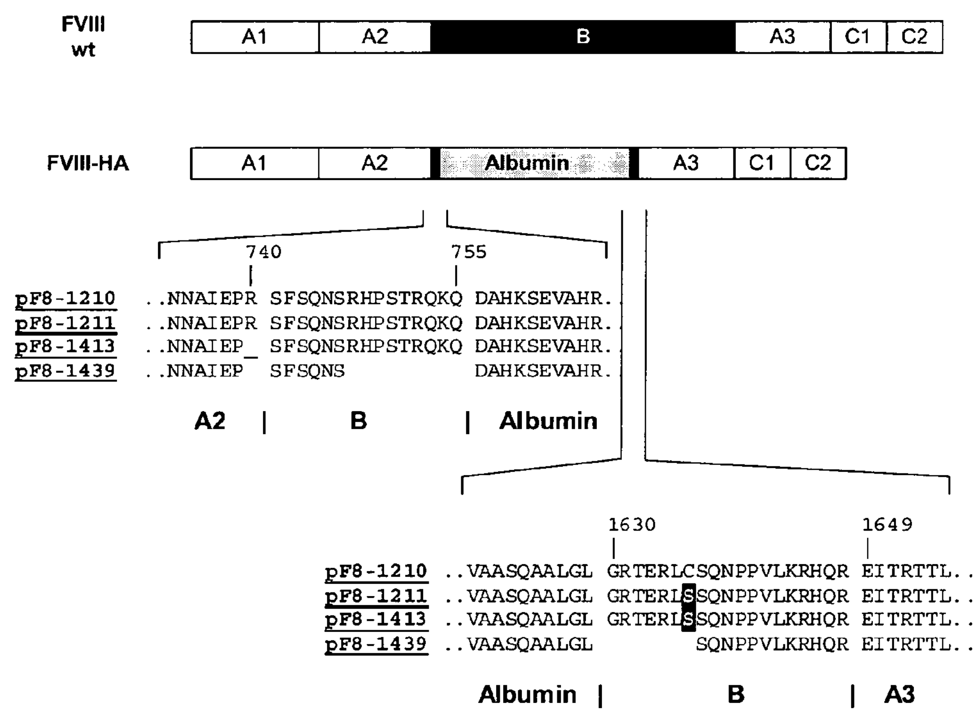

Figure 1b: Examples of B domain sequences used as linkers between the FVIII A2 domain and the B domain replacing HLEP (using albumin as the example for the HLEP moiety)

| A2 | B | Albumin | |
|---|---|---|---|
| NNAIEP | SFSQNSRHPSTRQKQ | DAHKSEVAHR | (SEQ ID NO. 23) |
| NNAIEPR | SFSQNSRHPSTRQKQ | DAHKSEVAHR | (SEQ ID NO. 24) |
| NNAIEPR | SFSQNSRHPSTRQ | DAHKSEVAHR | (SEQ ID NO. 25) |
| NNAIEPR | SFSQNSRHPST | DAHKSEVAHR | (SEQ ID NO. 26) |
| NNAIEPR | SFSQNSRH | DAHKSEVAHR | (SEQ ID NO. 27) |
| NNAIEPR | SFSQNS | DAHKSEVAHR | (SEQ ID NO. 28) |
| NNAIEPR | SFS | DAHKSEVAHR | (SEQ ID NO. 29) |

Figure 1c: Examples of other cleavable linker sequences between the FVIII A2 domain and the B domain replacing HLEP (using albumin as example)

| | | | |
|---|---|---|---|
| NNAIEPR | SFSQNSGGSGGSGGS | DAHKSEVAHR | (SEQ ID NO. 30) |
| NNAIEPR | SVAKKHPKTW | DAHKSEVAHR | (SEQ ID NO. 31) |
| NNAIEPR | SFQKKTRHYF | DAHKSEVAHR | (SEQ ID NO. 32) |
| NNAIEPR | AVGG | DAHKSEVAHR | (SEQ ID NO. 33) |

Figure 1d: Examples of B domain sequences used as linkers between the B domain replacing HLEP (using albumin as example) and the FVIII A3 domain

```
Albumin    |          B            |   A3
VAASQAALGL GRTERLCSQNPPVLKRHQR EITRTTL (SEQ ID NO. 34)
VAASQAALGL GRTERLSSQNPPVLKRHQR EITRTTL (SEQ ID NO. 35)
VAASQAALGL     TERLCSQNPPVLKRHQR EITRTTL (SEQ ID NO. 36)
VAASQAALGL     TERLSSQNPPVLKRHQR EITRTTL (SEQ ID NO. 37)
VAASQAALGL         LCSQNPPVLKRHQR EITRTTL (SEQ ID NO. 38)
VAASQAALGL         LSSQNPPVLKRHQR EITRTTL (SEQ ID NO. 39)
VAASQAALGL           SQNPPVLKRHQR EITRTTL (SEQ ID NO. 40)
VAASQAALGL                 VLKRHQR EITRTTL (SEQ ID NO. 41)
VAASQAALGL                     RHQR EITRTTL (SEQ ID NO. 42)
VAASQAALGL GRTERLCSQNPPVLKRHRR EITRTTL (SEQ ID NO. 43)
VAASQAALGL           SQNPPVLKRHRR EITRTTL (SEQ ID NO. 44)
VAASQAALGL                     RHRR EITRTTL (SEQ ID NO. 45)
VAASQAALGL                          EITRTTL (SEQ ID NO. 49)
```

Figure 1e: Examples of other linker sequences between the B domain replacing HLEP (using albumin as example) and the FVIII A3 domain

```
Albumin    |          B            |   A3
VAASQAALGL GGSGGSGGSGGSGGSRHRR EITRTTL (SEQ ID NO. 46)
VAASQAALGL     GGSGGSGGSGGSRHRR EITRTTL (SEQ ID NO. 47)
VAASQAALGL           GGSGGSRHRR EITRTTL (SEQ ID NO. 48)
```

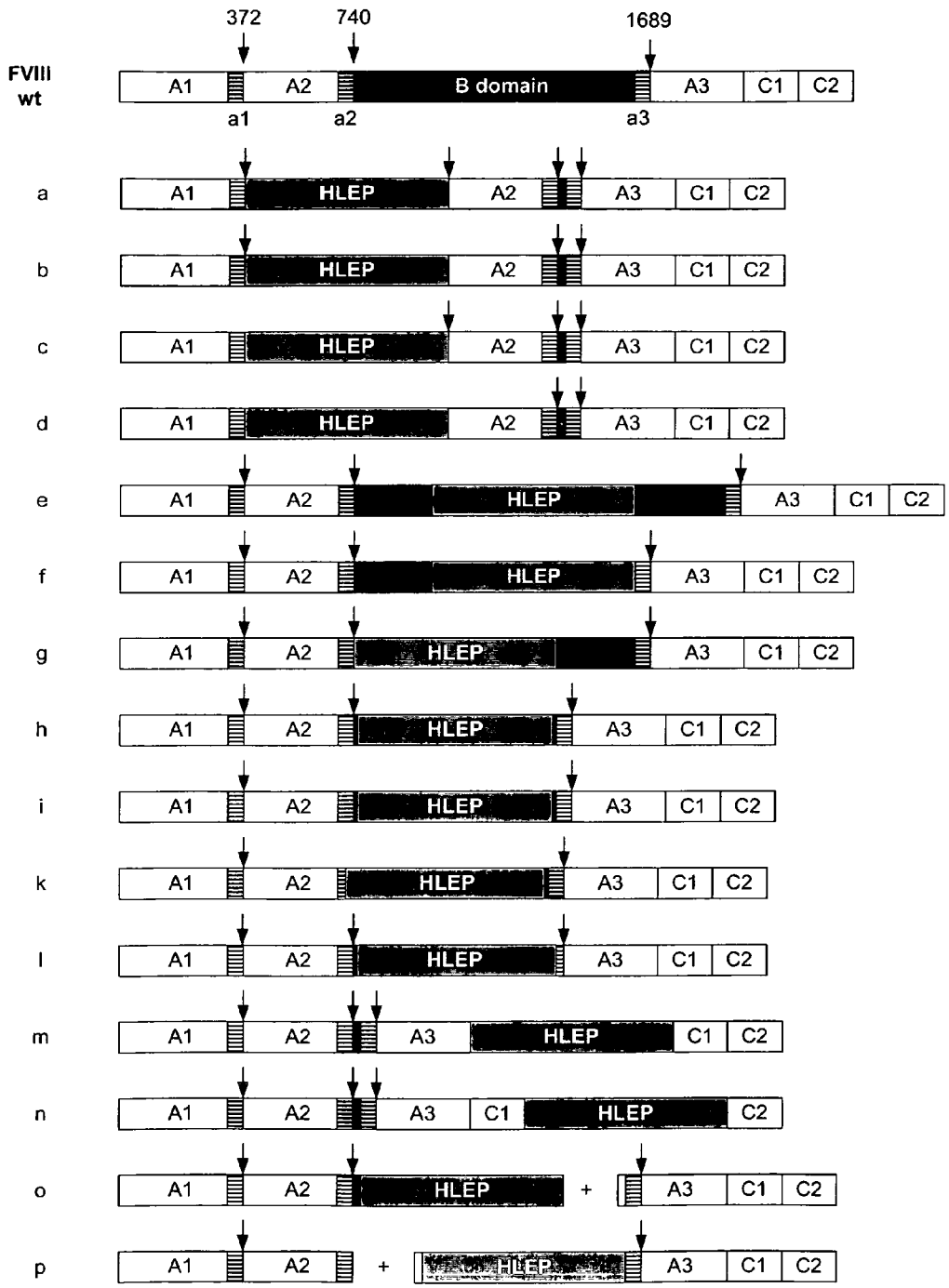
Figure 2: Examples of HLEP insertions within the FVIII molecule. Arrows denote cleavage sites.

Figure 3. Pharmacokinetic analysis in rats of FVIII mutants having the B domain replaced by human albumin in comparison to wild-type FVIII (Helixate®).
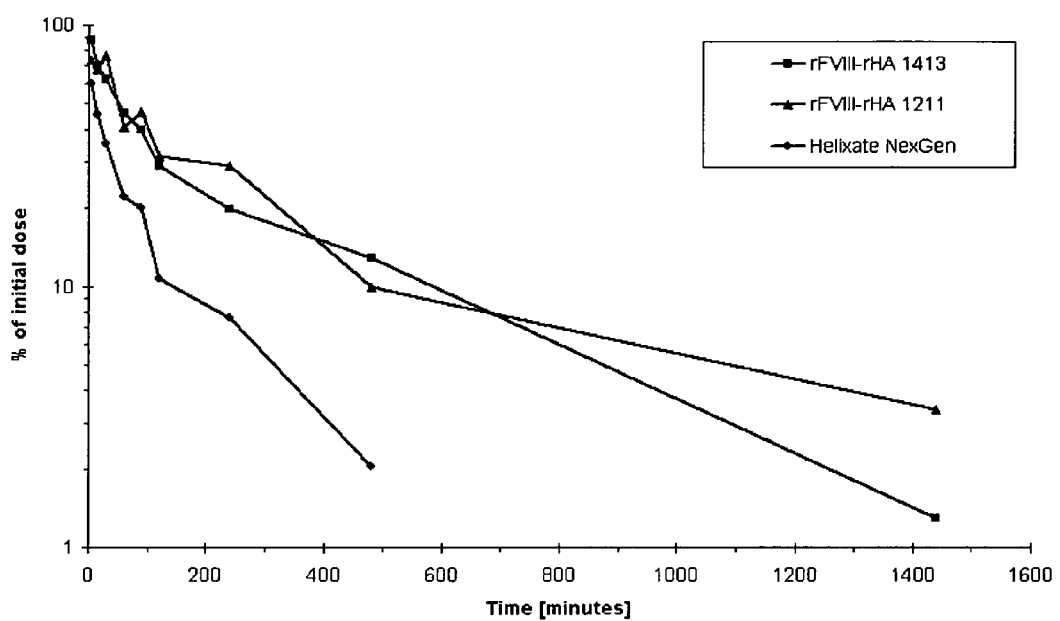

Figure 4. Analysis of cell culture supernatants at 3 time points after cell seeding (96, 120 and 144 hrs). HEK-293 transfectant pools were assessed for productivity of FVIII clotting activity and FVIII antigen and their ratios of a wild-type FVIII (457) and a FVIII mutant with B domain replacement by human albumin.
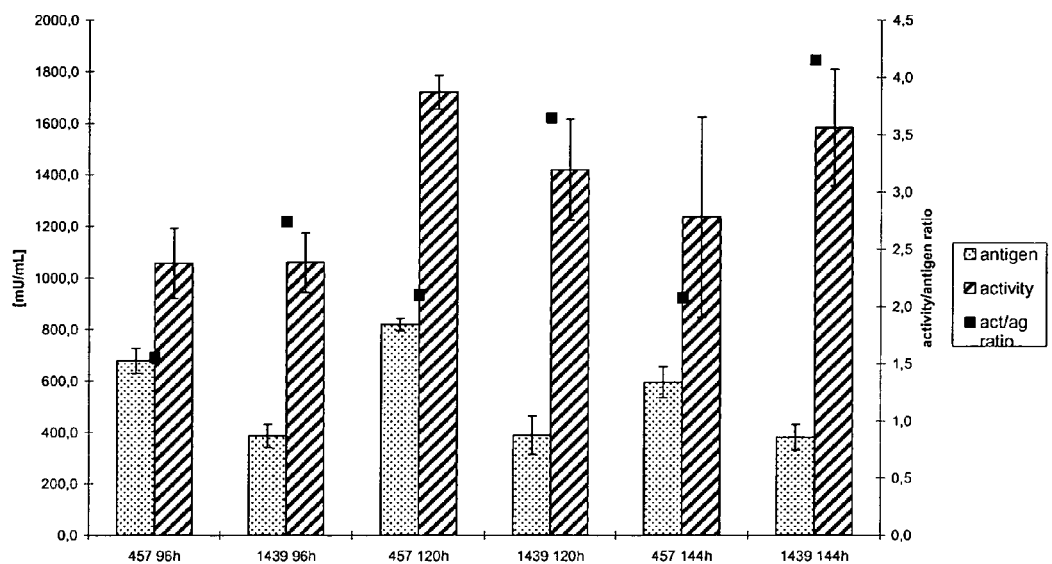

MODIFIED COAGULATION FACTORS WITH PROLONGED IN VIVO HALF-LIFE

CROSS REFERENCE TO RELATED APPLICATIONS

This application is a national stage filing under 35 U.S.C. §371 of International Application No. PCT/EP2007/011356, filed on Dec. 21, 2007, and claims the benefit of priority of European Application No. 06026747.3, filed on Dec. 22, 2006, and U.S. Provisional Application No. 60/879,334, filed on Jan. 9, 2007. All of these applications are incorporated herein by reference in their entirety.

FIELD OF THE INVENTION

The present invention relates to nucleic acid sequences coding for modified coagulation factors, preferably coagulation factor VIII, and their derivatives, recombinant expression vectors containing such nucleic acid sequences, host cells transformed with such recombinant expression vectors, and recombinant polypeptides and derivatives coded for by said nucleic acid sequences, wherein said recombinant polypeptides and derivatives have biological activities together with prolonged in vivo half-life and/or improved in vivo recovery compared to the unmodified wild-type proteins. The invention also relates to corresponding sequences that result in improved in vitro stability. The present invention further relates to processes for the manufacture of such recombinant proteins and their derivatives. The invention also relates to a transfer vector for use in human gene therapy, which comprises such nucleic acid sequences.

BACKGROUND OF THE INVENTION

There are various bleeding disorders caused by deficiencies of blood coagulation factors. The most common disorders are hemophilia A and B, resulting from deficiencies of blood coagulation factor VIII and IX, respectively. Another known bleeding disorder is von Willebrand's disease.

Classic hemophilia or hemophilia A is an inherited bleeding disorder. It results from a chromosome X-linked deficiency of blood coagulation Factor VIII, and affects almost exclusively males with an incidence of between one and two individuals per 10.000. The X-chromosome defect is transmitted by female carriers who are not themselves hemophiliacs. The clinical manifestation of hemophilia A is an increased bleeding tendency. Before treatment with Factor VIII concentrates was introduced the mean life span for a person with severe hemophilia was less than 20 years. The use of concentrates of Factor VIII from plasma has considerably improved the situation for the hemophilia A patients increasing the mean life span extensively, giving most of them the possibility to live a more or less normal life. However, there have been certain problems with the plasma derived concentrates and their use, the most serious of which have been the transmission of viruses. So far, viruses causing hepatitis B, non-A non-B hepatitis and AIDS have hit the population seriously. Since then different virus inactivation methods and new highly purified Factor VIII concentrates have recently been developed which established a very high safety standard also for plasma derived Factor VIII.

The cloning of the cDNA for Factor VIII (Wood et al. 1984. Nature 312:330-336; Vehar et al. 1984. Nature 312:337-342) made it possible to express Factor VIII recombinantly leading to the development of several recombinant Factor VIII products, which were approved by the regulatory authorities between 1992 and 2003. The fact that the central B domain of the Factor VIII polypeptide chain residing between amino acids Arg-740 and Glu-1649 does not seem to be necessary for full biological activity has also led to the development of a B domain deleted Factor VIII.

The mature Factor VIII molecule consists of 2332 amino acids which can be grouped into three homologous A domains, two homologous C domains and a B Domain which are arranged in the order: A1-A2-B-A3-C1-C2. The complete amino acid sequence of mature human Factor VIII is shown in SEQ ID NO:2. During its secretion into plasma Factor VIII is processed intracellularly into a series of metal-ion linked heterodimers as single chain Factor VIII is cleaved at the B-A3 boundary and at different sites within the B-domain. This processing leads to heterogenoeous heavy chain molecules consisting of the A1, the A2 and various parts of the B-domain which have a molecular size ranging from 90 kDa to 200 kDa. The heavy chains are bound via a metal ion to the light chains, which consist of the A3, the C1 and the C2 domain (Saenko et al. 2002. Vox Sang. 83:89-96). In plasma this heterodimeric Factor VIII binds with high affinity to von Willebrand Factor (vWF), which protects it from premature catabolism. The half-life of non-activated Factor VIII bound to vWF is about 12 hours in plasma.

Coagulation Factor VIII is activated via proteolytic cleavage by FXa and thrombin at amino acids Arg372 and Arg740 within the heavy chain and at Arg1689 in the light chain resulting in the release of von Willebrand Factor and generating the activated Factor VIII heterotrimer which will form the tenase complex on phospholipid surfaces with FIXa and FX provided that $Ca^{2+}$ is present. The heterotrimer consists of the A1 domain, a 50 kDa fragment, the A2 domain, a 43 kDa fragment and the light chain (A3-C1-C2), a 73 kDa fragment. Thus the active form of Factor VIII (Factor VIIIa) consists of an A1-subunit associated through the divalent metal ion linkage to a thrombin-cleaved A3-C1-C2 light chain and a free A2 subunit relatively loosely associated with the A1 and the A3 domain.

To avoid excessive coagulation, Factor VIIIa must be inactivated soon after activation. The inactivation of Factor VIIIa via activated Protein C (APC) by cleavage at Arg336 and Arg562 is not considered to be the major rate-limiting step. It is rather the dissociation of the non covalently attached A2 subunit from the heterotrimer which is thought to be the rate limiting step in Factor VIIIa inactivation after thrombin activation (Fay et al. 1991. J. Biol. Chem. 266 8957, Fay & Smudzin 1992. J. Biol. Chem. 267:13246-50). This is a rapid process, which explains the short half-life of Factor VIIIa in plasma, which is only 2.1 minutes (Saenko et al. 2002. Vox Sang. 83:89-96).

In severe hemophilia A patients undergoing prophylactic treatment Factor VIII has to be administered intravenously (i.v.) about 3 times per week due to the short plasma half-life of Factor VIII of about 12 hours. Each i.v. administration is cumbersome, associated with pain and entails the risk of an infection especially as this is mostly done at home by the patients themselves or by the parents of children being diagnosed for hemophilia A.

It would thus be highly desirable to create a Factor VIII with increased functional half-life allowing the manufacturing of pharmaceutical compositions containing Factor VIII, which have to be administered less frequently.

Several attempts have been made to prolong the half-life of non-activated Factor VIII either by reducing its interaction with cellular receptors (WO 03/093313A2, WO 02/060951A2), by covalently attaching polymers to Factor VIII (WO 94/15625, WO 97/11957 and U.S. Pat. No. 4,970, 300) or by encapsulation of Factor VIII (WO 99/55306).

In WO 97/03193 it was speculated that the introduction of novel metal binding sites could stabilize Factor VIII and in particular mutants in which His or Met is substituted for any of Phe652, Tyr1786, Lys1818, Asp1840 and/or Asn1864. However no rationale was provided how to determine the success meaning the stabilization resulting from such modifications nor a rationale why the proposed amino acids were chosen. This approach remains speculative, as no further evidence was published since.

Another approach has been made in creating a Factor VIIIa, which is inactivation resistant by first covalently attaching the A2 domain to the A3 domain and secondly by mutating the APC cleavage sites (Pipe & Kaufman. 1997. PNAS 94:11851-11856, WO 97/40145 and WO 03/087355.). The underlying genetic construct was also used to produce transgenic animals as described in WO 021072023A2. The instant variant showed still 38% of its peak activity 4 h after thrombin activation but lacks the vWF binding domain since by fusing the A2 to the A3 domain this particular domain was deleted. For the reason that vWF binding significantly prolongs half-life of FVIII in vivo, it is to be expected that half-life of the non-activated form of the instant FVIII variant is compromised. The inventors themselves recognized this and tried to overcome the problem by adding an antibody which stablizes the light chain in a conformation which retains some affinity for vWF.

Gale et al. 2002 (Protein Science 11:2091-2101) published the stabilization of FVa by covalently attaching the A3 domain to the A2 domain. They identified two neighbouring amino acids according to structural predictions, one on the A2 domain and the other being located on the A3 domain, and replaced these two amino acids with cysteine residues, which formed a disulfide bridge during export into the endoplasmatic reticulum. The same approach was used to covalently attach via disulfide bridges the A2 to the A3 domain of Factor VIII (WO 02/103024A2). Such Factor VIII mutants with covalently attached A3 and A2 domains, thus stabilizing FVIIIa, retained about 90% of their initial highest activity for 40 minutes after activation whereas the activity of wild type Factor VIII quickly diminished to 10% of its initial highest activity. The Factor VIII mutants retained their 90% activity for additional 3 h without any further loss of activity (Gale et al. 2003. J. Thromb. Haemost. 1:1966-1971).

WO2006/108590 discloses several stabilized FVIII mutants characterized by the insertion of different peptidic linkers substituting the thrombin activation site at Arg372 also stabilizing the activated form of FVIII. The level of FVIII activity increased concomitantly with the length of the linker reaching a maximum when 99 amino acids (L99) were inserted. Using a chromogenic assay method, the FVIII activity detected with FVIII L99 was similar to FVIII WT. Activated FVIII L99 was almost stable during more than 1 hour.

As none of the above described approaches has yet resulted in an improved FVIII molecule applicable in patients there is an ongoing need to develop modified coagulation factor VIII molecules which exhibit prolonged half-life.

In view of a potential thrombogenic risk it is more desirable to prolong the half-life of the non-activated form of FVIII than that of FVIIIa.

Another problem generally encountered with rec FVIII production is poor yield. Various methods known to the man of the art have been tried, but have not resolved such problem of poor yield.

DESCRIPTION OF THE INVENTION

It is an objective of this invention to provide blood coagulation molecules with enhanced in vivo half-life.

It is another objective of this invention to provide blood coagulation molecules with improved in vivo recovery.

Another objective of the invention is that these modified blood coagulation molecules can be expressed by mammalian cells and retain their biological activity in the expressed modified proteins.

Another objective of the invention is to provide an improved yield by increased expression and/or increased stability of the coagulation molecules in mammalian cell culture.

Yet another objective of the invention is to provide FVIII molecules with increased stability in mammalian cell culture in serum- and/or animal protein-free culture media, especially in the absence of vWF.

It was now surprisingly found that inserting heterologous polypeptides such as albumin into the FVIII molecule, preferably such that they replace the FVIII B domain almost completely or in part, not only permits expression and secretion of FVIII chimeric proteins from mammalian cells but also results in modified FVIII molecules that retain significant FVIII activity. In addition, such modified FVIII molecules exhibit prolonged in vivo half-life and/or improved in vivo recovery.

An additional potential benefit of those embodiments of the present invention in which FVIII is the coagulation factor and the A2 domain remains not covalently attached to the A3 domain after activation is that only the half-life of the non-activated form of FVIII is increased, whereas the half-life of the activated form of FVIII remains essentially the same, which might result in a decreased risk of thrombogenicity.

It was furthermore found that the FVIII molecules of the invention are more stable than wild-type FVIII in mammalian cell culture, especially in the absence of stabilizing von Willebrand factor (vWF) in serum- and/or animal protein-free culture media.

Such molecules can be generated by inserting a half-life enhancing protein (HLEP) moiety into the amino acid sequence of the blood coagulation factor, e.g. into the FVIII molecule. If FVIII is the blood coagulation factor the HLEP is preferably inserted into or replaces the B domain of FVIII or part of it.

HLEPs in the sense of the present invention are selected from a group consisting of members of the albumin family, which includes albumin, afamin, alpha-fetoprotein and the vitamin D binding protein, as well as portions of an immunoglobulin constant region and polypeptides capable of binding under physiological conditions to members of the albumin family as well as to portions of an immunoglobulin constant region. The most preferred HLEP is human albumin.

Also encompassed by the invention are other proteins in which HLEPs are inserted into other coagulation factors such as von Willebrand factor, factor V and prothrombin factors including factor VII, factor IX, factor X, protein C, protein S, protein Z and prothrombin. Similar to FVIII described above the particular HLEP, preferably albumin, is inserted in preferred embodiments at or in the vicinity of junction sites of domains or subunits of the coagulation factors above.

In the prior art fusions of coagulation factors to albumin (WO 01/79271), alpha-fetoprotein (WO 2005/024044) and immunoglobulin (WO 2004/101740) as half-life enhancing polypeptides have been described. These were taught to be attached to the carboxy- or the amino-terminus or to both termini of the respective therapeutic protein moiety, occasionally linked by peptidic linkers, preferably by linkers consisting of glycine and serine.

Ballance et al. (WO 01/79271) described N- or C-terminal fusion polypeptides of a multitude of different therapeutic polypeptides fused to human serum albumin. Long lists of potential fusion partners are described without disclosing experimental data for almost any of these polypeptides whether or not the respective albumin fusion proteins actually retain biological activity and have improved properties. Among said list of therapeutic polypeptides also Factor VIII is mentioned.

Contrary to prior art fusion proteins, the heterologous amino acid sequence in the modified coagulation factor of this invention is not fused to the very N-terminus or C-terminus of the coagulation factor, but inserted within an internal region of the amino acid sequence of the coagulation factor. Surprisingly, the insertion of even large polypeptides did not result in a complete loss of biological activity of the coagulation factor. Rather, the thus modified coagulation factor had biological activity, increased in vivo functional half-life, in vivo recovery and increased stability.

The present invention therefore relates to a modified coagulation factor having at an internal region of the coagulation factor an insertion of a half-life enhancing polypeptide (HLEP), characterized in that the modified coagulation factor has prolonged functional half-life compared to the functional half-life of the coagulation factor lacking said insertion, and/or compared to the functional half-life of the wild type coagulation factor.

The present invention also relates to the insertion of more than one HLEP wherein the HLEP, which is inserted several times, may be the same HLEP or may be a combination of different HLEPs. Also combinations of insertions of one or more HLEPs at an internal region of the coagulation factor with additional N- and/or C-terminal fusions of one or more HLEPs, which could be the same HLEP or a combination of different HLEPs are encompassed by the invention.

The present invention also relates to a modified coagulation factor having at an internal region of the coagulation factor an insertion of a half-life enhancing polypeptide (HLEP), characterized in that the modified coagulation factor has improved in vivo recovery compared to the in vivo recovery of the coagulation factor lacking said insertion, and/or compared to the in vivo recovery of the wild type coagulation factor.

In another aspect of the invention the modified coagulation factor has increased stability in serum-free culture media, compared to that of the coagulation factor lacking said insertion, and/or compared to the stability of the wild type coagulation factor. In another aspect of the invention the modified coagulation factor has increased stability in animal protein-free culture media, compared to that of the coagulation factor lacking said insertion, and/or compared to the stability of the wild type coagulation factor. The increased stability in serum-free and/or animal-free culture media is especially pronounced if stabilizing amounts of vWF are missing.

Animal protein-free media in the sense of the invention are media free from proteins or protein fragments derived from animals.

Another aspect of the invention are polynucleotides or sets of polynucleotides encoding the modified coagulation factor of the invention.

The invention further relates to plasmids or vectors comprising a polynucleotide described herein, to host cells comprising a polynucleotide or a plasmid or vector described herein.

Another aspect of the invention is a method of producing a modified coagulation factor, comprising:

(a) culturing host cells of the invention under conditions such that the modified coagulation factor is expressed; and (b) optionally recovering the modified coagulation factor from the host cells or from the culture medium.

The invention further pertains to pharmaceutical compositions comprising a modified coagulation factor, a polynucleotide, or a plasmid or vector described herein.

Yet another aspect of the invention is the use of a modified coagulation factor, a polynucleotide, or a plasmid or vector, or of a host cell according to this invention for the manufacture of a medicament for the treatment or prevention of a blood coagulation disorder.

DETAILED DESCRIPTION OF THE INVENTION

The invention pertains to a modified coagulation factor comprising at an internal region between the N-terminal amino acid and the C-terminal amino acid of the primary translation polypeptide of the coagulation factor an insertion of a half-life enhancing polypeptide (HLEP), characterized in that the modified coagulation factor has prolonged functional half-life compared to the functional half-life of the coagulation factor lacking said insertion, and/or compared to the functional half-life of the wild type coagulation factor.

The "functional half-life" according to the present invention is the half-life of the biological function of the coagulation factor once it has been administered to a mammal and can be measured in vitro in blood samples taken at different time intervals from said mammal after the coagulation factors has been administered.

The phrases "insertion", "inserting" and "inserted" refer to the addition of amino acids at an internal position of the coagulation factor amino acid sequence. Other than in the case of N-terminal or C-terminal fusion proteins, the amino acids are according to this invention not added to the very N-terminus or C-terminus of the coagulation factor amino acid sequence, but inserted at an internal position within the amino acid sequence of the coagulation factor. "Insertion" encompasses not only the addition of amino acids (without deleting amino acids from the coagulation factor amino acid sequence), but also the replacement of one or more amino acids of the coagulation factor amino acid sequence with the amino acids to be "inserted". For example, a complete internal domain or a substantial part thereof may be replaced with the HLEP.

In one embodiment, the modified coagulation factor has the following structure:

$$N\text{-}L1\text{-}H\text{-}L2\text{-}C, \qquad \text{[formula 1]}$$

wherein

N is an N-terminal portion of a coagulation factor,

L1 and L2 independently are chemical bonds or linker sequences, which linker sequences can be different linker sequences or the same linker sequences, H is a HLEP, and C is a C-terminal portion of the coagulation factor.

Preferably, N comprises one or two or three or four or five protein domains that are present at the N-terminus of the wild type coagulation factor. C preferably comprises one or two or three or four or five protein domains that are present at the C-terminus of the wild type coagulation factor. In one embodiment, the wild type coagulation factor has substantially the structure N-C. In another embodiment, the wild type coagulation factor has substantially the structure N-D-C, wherein D represents a domain or a part thereof that is replaced with the HLEP in the modified coagulation factor or in other words D represents a deletion of a part of the wild type coagulation factor (i.e. a complete domain or part thereof) which is replaced with the HLEP in the modified coagulation factor. Preferred coagulation factor sequences are described infra. Usually, the length of N+C does not exceed that of the wild type coagulation factor.

L1 and L2 may independently be chemical bonds or linker sequences consisting of one or more amino acids, e.g. of 1 to 20, 1 to 15, 1 to 10, 1 to 5 or 1 to 3 (e.g. 1, 2 or 3) amino acids and which may be equal or different from each other. Usually, the linker sequences are not present at the corresponding position in the wild type coagulation factor. Examples of suitable amino acids present in L1 and L2 include Gly and Ser.

Preferred HLEP sequences are described infra. The modified coagulation factor of the invention may comprise more than one HLEP sequence, e.g. two or three HLEP sequences. These multiple HLEP sequences may be inserted in tandem, e.g. as successive repeats, or they may be present at different positions of the coagulation factor sequence including also fusions of HLEP sequences at the very N-terminus or at the very C-terminus or at both termini of the coagulation factor sequence, wherein at least one HLEP sequence must be inserted at an internal position within the coagulation factor sequence. In these embodiments, the modified coagulation factor may have one of the following structures:

N-L1-H-L2-I-L3-H-L4-C  [formula 2]

N-L1-H-L2-C-L3-H  [formula 3]

H-L1-N-L2-H-L3-C  [formula 4]

H-L1-N-L2-H-L3-C-L4-H  [formula 5]

wherein
N is an N-terminal portion of a coagulation factor,
L1, L2, L3 and L4 independently are chemical bonds or linker sequences, which linker sequences can be different linker sequences or the same linker sequences,
H is a HLEP,
I is an internal sequence of the coagulation factor and
C is a C-terminal portion of the coagulation factor.

Coagulation factors may be processed proteolytically at various stages. For example, as mentioned supra, during its secretion, into plasma single chain Factor VIII is cleaved intracellularly at the B-A3 boundary and at different sites within the B-domain. The heavy chain is bound via a metal ion to the light chain having the domain structure A3-C1-C2. Factor VIII is activated via proteolytic cleavage at amino acids Arg372 and Arg740 within the heavy chain and at Arg1689 in the light chain generating the activated Factor VIII heterotrimer consisting of the A1 domain, the A2 domain, and the light chain (A3-C1-C2), a 73 kDa fragment. Thus the active form of Factor VIII (Factor VIIIa) consists of an A1-subunit associated through the divalent metal ion linkage to a thrombin-cleaved A3-C1-C2 light chain and a free A2 subunit relatively loosely associated with the A1 and the A3 domain.

Accordingly, the present invention encompasses also modified coagulation factors that are not present as single chain polypeptides but consist of several polypeptides (e.g. one or two or three) that are associated with each other via non-covalent linkages. By way of example, the structure of the modified coagulation factor may be as follows:

N-L1-H-L2 . . . C,  [formula 6]

N-L1-H . . . L2-C,  [formula 7]

N-L1-H-L2-C,  [formula 8]

N . . . L1-H-L2-C,  [formula 9]

wherein " . . . " signifies a non-covalent linkage, and the meaning of N, L1, L2, H and C is as defined above. Cleaved forms analogous to those of formula 6 to formula 9 of polypeptides according to formula 2 to formula 5 are also encompassed by the invention.

Usually, the site of insertion is chosen such that the biological activity of the coagulation factor is retained in full or at least in part. Preferably, the biological activity of the modified coagulation factor of the invention is at least 25%, more preferably at least 50%, most preferably at least 75% of biological activity of the coagulation factor lacking the insertion or of the wild type form of the coagulation factor.

Generally, insertion between two domains of the coagulation factor or within the vicinity of the boundary between two domains is preferred. The two domains may be adjacent domains in the wild type coagulation factor or not.

When referring herein to an insertion between two domains (e.g. an "insertion between domain X and domain Y"), this preferably means an insertion exactly between the C-terminal amino acid of domain X and the N-terminal amino acid of domain Y. However, an "insertion between domain X and domain Y" in the sense of this invention may also include an insertion at an amino acid position up to n amino acids upstream to the C-terminal amino acid of domain X, or at an amino acid position up to n amino acids downstream to the N-terminal amino acid of domain Y. The figure n is an integer that should not be greater than 10%, preferably not greater than 5% of the total number of amino acids of the domain referred to. Usually, n is 20, preferably 15, more preferably 10, still more preferably 5 or less (e.g. 1, 2, 3, 4 or 5).

It is also preferred that the stability of the modified coagulation factor in serum-free medium is greater than that of the coagulation factor lacking the insertion and/or that of the wild type form of the coagulation factor. It is also preferred that the stability of the modified coagulation factor in animal protein-free medium is greater than that of the coagulation factor lacking the insertion and/or that of the wild type form of the coagulation factor. Preferably the increase in stability compared to the coagulation factor lacking the insertion and/or to the wild type form of the coagulation factor is at least 10%, more preferably at least 25%, most preferably at least 50%. The stability of the coagulation factor in those media can be determined as described in example 7.

The functional half-life according to the present invention is the half-life of the biological function of the coagulation factor once it has been administered to a mammal and is measured in vitro. The functional half-life of the modified coagulation factor according to the invention is greater than that of the coagulation factor lacking the modification as tested in the same species. The functional half-life is preferably increased by at least 25%, more preferably by at least 50%, and even more preferably by at least 100% compared to the coagulation factor lacking the modification and/or to the wild type form of the coagulation factor.

The functional half-life of a modified coagulation factor comprising a HLEP modification, can be determined by administering the respective modified coagulation factor (and in comparison that of the non-modified coagulation factor) to rats, rabbits or other experimental animal species intravenously or subcutaneously and following the elimination of the biological activity of said modified or respectively non-modified coagulation factor in blood samples drawn at appropriate intervals after application. Suitable test methods are the activity tests described herein.

As a surrogate marker for the half-life of biological activity also the levels of antigen of the modified or respectively non-modified coagulation factor can be measured. Thus also encompassed by the invention are modified coagulation factors having at an internal region between the N-terminal amino acid and the C-terminal amino acid of the primary translation polypeptide of the coagulation factor an insertion of a half-life enhancing polypeptide (HLEP), characterized in that the modified coagulation factor has a prolonged half-life of the coagulation factor antigen compared to the half-life of the coagulation factor antigen lacking said insertion. The "half-life of the coagulation factor antigen" according to the present invention is the half-life of the antigen of the coagulation factor once it has been administered to a mammal and is measured in vitro. Antigen test methods based on specific antibodies in an enzyme immunoassay format as known to the man of the art and commercially available (e.g. Dade Behring, Instrumentation Laboratory, Abbott Laboratories, Diagnostica Stago). Functional and antigen half-lives can be calculated using the time points of the beta phase of elimination according to the formula $t_{1/2}=\ln2/k$, whereas k is the slope of the regression line.

Once a coagulation factor is activated in vivo during coagulation, it may be no longer desirable to maintain the increased half-life of the now activated coagulation factor as this might lead to thrombotic complications what is already the case for a wild type activated coagulation factor FVIIa (Aledort 2004. J Thromb Haemost 2:1700-1708) and what should be much more possibly threatening if the activated factor would have an increased half-life. It is therefore another objective of the present invention to provide long-lived coagulation factor molecules, which after endogenous activation in vivo or after availability of a cofactor in vivo do have a functional half-life comparable to that of an unmodified coagulation factor. This can be achieved by maintaining certain cleavage sites in the modified coagulation factor (see infra) leading to a proteolytic cleavage during activation which separates the coagulation factor from the HLEP. Accordingly, in one embodiment, the functional half-life of the endogenously activated modified coagulation factor is substantially the same as that of the activated non-modified coagulation factor lacking the modification, and/or it is substantially the same as that of the activated wild type coagulation factor (e.g. ±15%, preferably ±10%).

In another embodiment, the functional half-life of the endogenously activated modified coagulation factor is prolonged compared to that of the activated non-modified coagulation factor lacking the insertion, or compared to that of the activated wild type coagulation factor. The increase may be more than 15%, for example at least 20% or at least 50%. Again, such functional half-life values can be measured and calculated as described for functional half-lives supra. Increased half-lives of the endogenously activated modified coagulation factors may be beneficial in situations were only very low levels of the coagulation factors are available that therefore are not thrombogenic. Such situations may occur e.g. upon gene therapy treatment where often only low expression rates can be achieved. Therefore, such stabilized coagulation factors might be beneficial in e.g. gene therapy despite a thrombogenic risk connected to such coagulation factors if administered as proteins in high or physiologic doses.

Half-Life Enhancing Polypeptides (HLEPs)

A "half-life enhancing polypeptide" as used herein is selected from the group consisting of albumin, a member of the albumin-family, the constant region of immunoglobulin G and fragments thereof and polypeptides capable of binding under physiological conditions to albumin, to members of the albumin family as well as to portions of an immunoglobulin constant region. It may be a full-length half-life-enhancing protein described herein (e.g. albumin, a member of the albumin-family or the constant region of immunoglobulin G) or one or more fragments thereof that are capable of stabilizing or prolonging the therapeutic activity or the biological activity of the coagulation factor. Such fragments may be of 10 or more amino acids in length or may include at least about 15, at least about 20, at least about 25, at least about 30, at least about 50, at least about 100, or more contiguous amino acids from the HLEP sequence or may include part or all of specific domains of the respective HLEP, as long as the HLEP fragment provides a functional half-life extension of at least 25% compared to a wild type coagulation factor.

The HLEP portion of the proposed coagulation factor insertion constructs of the invention may be a variant of a normal HLEP. The term "variants" includes insertions, deletions and substitutions, either conservative or non-conservative, where such changes do not substantially alter the active site, or active domain which confers the biological activities of the modified coagulation factors.

In particular, the proposed FVIII HLEP insertion or B domain replacement constructs of the invention may include naturally occurring polymorphic variants of HLEPs and fragments of HLEPs. The HLEP may be derived from any vertebrate, especially any mammal, for example human, monkey, cow, sheep, or pig. Non-mammalian HLEPs include, but are not limited to, hen and salmon.

Albumin as HLEP

The terms, "human serum albumin" (HSA) and "human albumin" (HA) and "albumin" (ALB) are used interchangeably in this application. The terms "albumin" and "serum albumin" are broader, and encompass human serum albumin (and fragments and variants thereof) as well as albumin from other species (and fragments and variants thereof).

As used herein, "albumin" refers collectively to albumin polypeptide or amino acid sequence, or an albumin fragment or variant, having one or more functional activities (e.g., biological activities) of albumin. In particular, "albumin" refers to human albumin or fragments thereof, especially the mature form of human albumin as shown in SEQ ID NO:3 herein or albumin from other vertebrates or fragments thereof, or analogs or variants of these molecules or fragments thereof.

In particular, the proposed coagulation factor insertion constructs of the invention may include naturally occurring polymorphic variants of human albumin and fragments of human albumin. Generally speaking, an albumin fragment or variant will be at least 10, preferably at least 40, most preferably more than 70 amino acids long. The albumin variant may preferentially consist of or alternatively comprise at least one whole domain of albumin or fragments of said domains, for example domains 1 (amino acids 1-194 of SEQ ID NO:3), 2 (amino acids 195-387 of SEQ ID NO: 3), 3 (amino acids 388-585 of SEQ ID NO: 3), 1+2 (1-387 of SEQ ID NO: 3), 2+3 (195-585 of SEQ ID NO: 3) or 1+3 (amino acids 1-194 of SEQ ID NO: 3+amino acids 388-585 of SEQ ID NO: 3). Each domain is itself made up of two homologous subdomains namely 1-105, 120-194, 195-291, 316-387, 388-491 and 512-585, with flexible inter-subdomain linker regions comprising residues Lys106 to Glu119, Glu292 to Val315 and Glu492 to Ala511.

The albumin portion of the proposed coagulation factor insertion constructs of the invention may comprise at least one subdomain or domain of HA or conservative modifications thereof.

Afamin, Alpha-Fetoprotein and Vitamin D Binding Protein as HLEPs

Besides albumin, alpha-fetoprotein, another member of the albumin family, has been claimed to enhance the half-life of an attached therapeutic polypeptide in vivo (WO 2005/024044). The albumin family of proteins, evolutionarily related serum transport proteins, consists of albumin, alpha-fetoprotein (AFP; Beattie & Dugaiczyk 1982. Gene 20:415-422), afamin (AFM; Lichenstein et al. 1994. J. Biol. Chem. 269:18149-18154) and vitamin D binding protein (DBP; Cooke & David 1985. J. Clin. Invest. 76:2420-2424). Their genes represent a multigene cluster with structural and functional similarities mapping to the same chromosomal region in humans, mice and rat. The structural similarity of the albumin family members suggest their usability as HLEPs. It is therefore another object of the invention to use such albumin family members, fragments and variants thereof as HLEPs. The term "variants" includes insertions, deletions and substitutions, either conservative or non-conservative as long as the desired function is still present.

Albumin family members may comprise the full length of the respective protein AFP, AFM and DBP, or may include one or more fragments thereof that are capable of stabilizing or prolonging the therapeutic activity. Such fragments may be of 10 or more amino acids in length or may include about 15, 20, 25, 30, 50, or more contiguous amino acids of the respective protein sequence or may include part or all of specific domains of the respective protein, as long as the HLEP fragments provide a half-life extension of at least 25%. Albumin family members of the insertion proteins of the invention may include naturally occurring polymorphic variants of AFP, AFM and DBP.

Immunoglobulins as HLEPs

Immunoglobulin G (IgG) constant regions (Fc) are known in the art to increase the half-life of therapeutic proteins (Dumont J A et al. 2006. BioDrugs 20:151-160). The IgG constant region of the heavy chain consists of 3 domains (CH1-CH3) and a hinge region. The immunoglobulin sequence may be derived from any mammal, or from subclasses IgG1, IgG2, IgG3 or IgG4, respectively. IgG and IgG fragments without an antigen-binding domain may also be used as HLEPs. The therapeutic polypeptide portion is connected to the IgG or the IgG fragments preferably via the hinge region of the antibody or a peptidic linker, which may even be cleavable. Several patents and patent applications describe the fusion of therapeutic proteins to immunoglobulin constant regions to enhance the therapeutic protein's in vivo half-lifes. US 2004/0087778 and WO 2005/001025 describe fusion proteins of Fc domains or at least portions of immunoglobulin constant regions with biologically active peptides that increase the half-life of the peptide, which otherwise would be quickly eliminated in vivo. Fc-IFN-β fusion proteins were described that achieved enhanced biological activity, prolonged circulating half-life and greater solubility (WO 2006/000448). Fc-EPO proteins with a prolonged serum half-life and increased in vivo potency were disclosed (WO 2005/063808) as well as Fc fusions with G-CSF (WO 2003/076567), glucagon-like peptide-1 (WO 2005/000892), clotting factors (WO 2004/101740) and interleukin-10 (U.S. Pat. No. 6,403,077), all with half-life enhancing properties.

Coagulation Factors

The term "coagulation factor" as used herein denotes a blood coagulation factor or blood clotting factor. Coagulation factors include factor VIII, von Willebrand factor, prothrombin factors (comprising factor VII, Factor IX, factor X, protein C, protein S, protein Z and prothrombin) and coagulation factor V.

Coagulation factors of the present invention may also be variants of wild-type coagulation factors. The term "variants" includes insertions, deletions and substitutions, either conservative or non-conservative, where such changes do not substantially alter the active site, or active domain, which confers the biological activities of the respective coagulation factor.

FVIII

The terms "blood coagulation Factor VIII", "Factor VIII" and FVIII" are used interchangeably herein. "Blood coagulation Factor VIII" includes wild type blood coagulation Factor VIII as well as derivatives of wild type blood coagulation Factor VIII having the procoagulant activity of wild type blood coagulation Factor VIII. Derivatives may have deletions, insertions and/or additions compared with the amino acid sequence of wild type Factor VIII. The term FVIII includes proteolytically processed forms of Factor VIII, e.g. the form before activation, comprising heavy chain and light chain.

The term "Factor VIII" includes any Factor VIII variants or mutants having at least 10%, preferably at least 25%, more preferably at least 50%, most preferably at least 75% of the biological activity of wild type factor VIII.

As non-limiting examples, Factor VIII molecules include Factor VIII mutants preventing or reducing APC cleavage (Amano 1998. Thromb. Haemost. 79:557-563), Factor VIII mutants further stabilizing the A2 domain (WO 97/40145), FVIII mutants resulting in increased expression (Swaroop et al. 1997. JBC 272:24121-24124), Factor VIII mutants reducing its immunogenicity (Lollar 1999. Thromb. Haemost. 82:505-508), FVIII reconstituted from differently expressed heavy and light chains (Oh et al. 1999. Exp. Mol. Med. 31:95-100), FVIII mutants reducing binding to receptors leading to catabolism of FVIII like HSPG (heparan sulfate proteoglycans) and/or LRP (low density lipoprotein receptor related protein) (Ananyeva et al. 2001. TCM, 11:251-257), disulfide bond-stabilized FVIII variants (Gale et al., 2006. J. Thromb. Hemost. 4:1315-1322), FVIII mutants with improved secretion properties (Miao et al., 2004. Blood 103: 3412-3419), FVIII mutants with increased cofactor specific activity (Wakabayashi et al., 2005. Biochemistry 44:10298-304), FVIII mutants with improved biosynthesis and secretion, reduced ER chaperone interaction, improved ER-Golgi transport, increased activation or resistance to inactivation and improved half-life (summarized by Pipe 2004. Sem. Thromb. Hemost. 30:227-237). All of these factor VIII mutants and variants are incorporated herein by reference in their entirety.

A suitable test to determine the biological activity of Factor VIII is the one stage or the two stage coagulation assay (Rizza et al. 1982. Coagulation assay of FVIII:C and FIXa in Bloom ed. The Hemophilias. NY Churchchill Livingston 1992) or the chromogenic substrate FVIII:C assay (S. Rosen, 1984. Scand J Haematol 33: 139-145, suppl.). The content of these references is incorporated herein by reference.

The cDNA sequence and the amino acid sequence of the mature wild type form of human blood coagulation Factor VIII are shown in SEQ ID NO:1 and SEQ ID NO:2, respectively. The reference to an amino acid position of a specific sequence means the position of said amino acid in the FVIII wild-type protein and does not exclude the presence of mutations, e.g. deletions, insertions and/or substitutions at other positions in the sequence referred to. For example, a mutation in "Glu2004" referring to SEQ ID NO:2 does not exclude that in the modified homologue one or more amino acids at positions 1 through 2332 of SEQ ID NO:2 are missing.

FVIII Proteins with a HLEP Insertion

Modified FVIII proteins of the invention in the most general sense are characterized in that they comprise FVIII molecules with a HLEP integrated into the FVIII molecules such that the HLEP does not reduce the molar specific FVIII activity of the chimeric protein below about 10% of the molar specific FVIII activity of wild type FVIII. The insertion of the HLEP can take place in any place between the N-terminal and the C-terminal amino acid of the FVIII sequence. Preferentially the HLEP is integrated between domains of the wild-type FVIII protein.

The domains of FVIII comprise the following amino acid positions (amino acid numbers refer to SEQ ID NO:2):

A1: . . . 1-336
a1: . . . 337-372
A2: . . . 373-710
a2: . . . 711-740
B: . . . 741-1648
a3: . . . 1649-1689
A3: . . . 1690-2019
C1: . . . 2020-2172
C2: . . . 2173-2332

Preferred integration sites for a HLEP within the FVIII molecule are defined as such sites where the insertion of a HLEP moiety has the least negative effect on FVIII functional activity. Potential integration sites include, but are not limited to, the region between the C-terminus of acidic region 1 (a1) and the N-terminus of the A2 domain, the region between the C-terminus of the A3 domain and the N-terminus of the C1 domain, the region between the C-terminus of the C1 domain and the N-terminus of the C2 domain and preferably the region of the B domain, where the B domain may be replaced partially or in its entirety (FIG. 2).

In a preferred embodiment of the invention chimeric FVIII proteins of the invention are characterized in that they comprise FVIII molecules with partial or full deletion of the B domain and a HLEP integrated into the FVIII molecules such that the HLEP is inserted between a functional A1/A2 domain at its amino terminus and a functional A3/C1/C2 domain at its carboxy terminus.

It was found that it is possible to insert HLEPs or HLEP derivatives within the B domain (the FVIII sequence between the A2 and A3 domains [amino acids 741 to 1648] which seems dispensable for the biological function of FVIII (Pittman et al. 1992. Blood 81:2925-2935) to provide FVIII molecules with new and improved properties while retaining FVIII biological activity. The B domain has a length of about 900 amino acids and the HLEP may either be inserted at any place within the B domain without any deletion of the B domain or the B domain may be replaced by a HLEP partially or in its entirety. Partial deletion refers to deletions of at least 1 amino acid, preferably to deletions of 100 to 600 amino acids and most preferred to deletions of more than 600 amino acids of the B domain (FIG. 2*e-h*).

In a preferred embodiment of the invention most of the B domain is replaced by a HLEP, while a few amino acids of the amino and carboxy terminal sequence of the B domain containing processing sites important for cleavage and activation of the FVIII molecules of the invention are conserved (FIGS. 1*a, b, d* and 2*h-i*). Preferably about 1 to 20 amino acids, more preferably 3 to 10 amino acids, at the C- and at the N-terminus of the B domain, which are required to conserve the processing sites for thrombin at amino acid position 740 of the FVIII sequence (SEQ ID NO 2) and the protease cleaving between the B domain and the A3 domain during the secretion process, are maintained within the FVIII molecule of the invention (FIG. 1 and FIG. 2*h*). Alternatively, the amino acids retained from the B domain might be replaced by artificial cleavage sites. A PACE/Furin cleavage site (Nakayama 1997. Biochem. J. 327:625-635) may be used to guide the processing during secretion, and artificial thrombin cleavage sites as described in WO 2004/005347 (FIG. 1*c*) or other protease cleavage sites may be introduced for activation processing (FIG. 1*e*).

Another aspect of the invention is the insertion of more than one HLEP wherein the HLEP, which is inserted several times, may be the same HLEP or may be a combination of different HLEPs. Also combinations of insertions of one or more HLEPs into FVIII with additional N- and/or C-terminal fusions of one or more HLEPs, which could be the same HLEP or a combination of different HLEPs are encompassed by the invention.

Once a coagulation factor is endogenously activated during coagulation in vivo, it may be no longer desirable to maintain the increased functional half-life of the now activated coagulation factor as this might lead to thrombotic complications what is already the case for a wild type activated coagulation factor as FVIIa (Aledort 2004. J Thromb Haemost 2:1700-1708) and what should be much more relevant if the activated factor would have an increased functional half-life. It is therefore another objective of the present invention to provide long-lived coagulation factor VIII molecules, which after endogenous activation in vivo or after availability of a cofactor do have a functional half-life comparable to that of unmodified FVIII. This can by way of non-limiting example be achieved by maintaining the cleavage sites for thrombin at amino acid position 740 of the FVIII sequence (SEQ ID NO 2) and for the protease cleaving between the B domain and the A3 domain during the secretion process. With such FVIII-HLEP connecting sequences the activation of the FVIII chimeric protein of the invention will lead to a concomitant complete separation of FVIIIa from the HLEP moiety.

In yet another embodiment of the invention, however, one or more of the proteolytical cleavage sites, preferably the thrombin cleavage sites at Arg740 (e.g. FIG. 2*i*) and/or Arg372, are mutated or deleted in order to prevent cleavage and result in an insertion protein which displays improved properties like enhanced functional half-life even as an activated molecule.

In another embodiment of the invention the deletion of the B domain may be extended into the flanking acidic regions a2 and a3 (FIGS. 2*k* and *l*). With regard to a2 this region may be deleted in part (FIG. 2*k*) or completely. Therefore the HLEP moiety will not be released upon FVIII activation but instead remain attached to the A2 domain. Such an activated insertion protein will have an enhanced functional half-life. Acidic region a3 may be deleted in part (FIG. 2*l*) as long as the vWF binding properties of a3 remain unaffected.

In one embodiment of the invention another potential integration site within the FVIII molecule is represented by the region between the C-terminus of acidic region 1 (a1)) and the N-terminus of the A2 domain (FIG. 2*a-d*). FIG. 2*a* describes an integration scheme where an additional thrombin cleavage site has been introduced at the albumin C-terminus. In such an insertion protein the HLEP moiety will be cleaved off during endogenous FVIII activation in vivo and the activated FVIII molecule will have a functional half-life comparable to wild-type FVIII. In the case of an insertion protein as depicted in FIG. 2*b* the additional thrombin cleavage site at the HLEP C-terminus is lacking. Therefore the HLEP will not be released upon FVIII activation but instead remain attached to the A2 domain. Such an activated insertion protein will have an enhanced functional half-life. In the case of an insertion protein as depicted in FIG. 2*c* the thrombin cleavage site at Arg372 is lacking. Therefore the HLEP will not be released upon FVIII activation but instead remain attached to the A1 domain. Such an activated insertion protein will have an enhanced half-life. An insertion protein as depicted in FIG. 2d will keep A1 and A2 domains covalently linked and generate an insertion protein with functional half-life extension also of the activated form.

In another embodiment of the invention another potential integration site within the FVIII molecule is represented by the region between the C-terminus of the A3 domain and the N-terminus of the C1 domain (FIG. 2m). In such an insertion protein the HLEP moiety will be an integral component of the FVIII light chain and both the non-activated and the activated insertion protein will have enhanced functional half-lives.

In another embodiment of the invention another potential integration site within the FVIII molecule is represented by the region between the C-terminus of the C1 domain and the N-terminus of the C2 domain (FIG. 2n). In such an insertion protein the HLEP moiety will be an integral component of the FVIII light chain and both the non-activated and the activated insertion protein will have enhanced functional half-lives.

In another embodiment of the invention the FVIII proteins of the invention may be expressed as two separate chains (see infra).

The modified coagulation factor VIII according to this invention may be a single chain polypeptide, or it may be composed of two or three polypeptide chains that are associated via non-covalent linkages, due to proteolytic processing.

In another embodiment of the invention, the amino acids at or near the PACE/Furin cleavage site (Arg1648, e.g. FIG. 1a) are mutated or deleted in order to prevent cleavage by PACE/Furin. This is thought to result in a one-chain Factor VIII/HLEP fusion molecule with improved half-life.

In one embodiment of the invention, the modified FVIII of the invention exhibits an increased functional half-life compared to the corresponding FVIII form containing no integrated HLEP and/or to the wild type form FVIII. The functional half-life e.g. can be determined in vivo in animal models of hemophilia A, like FVIII knockout mice, in which one would expect a longer lasting hemostatic effect as compared to wild type FVIII. The hemostatic effect could be tested for example by determining time to arrest of bleeding after a tail clip.

The functional half-life is preferably increased by at least 25%, more preferably by at least 50%, and even more preferably by at least 100% compared to the form without inclusion of a HLEP and/or to the wild type form of FVIII.

In another embodiment of the invention, the modified FVIII of the invention exhibits an improved in vivo recovery compared to the corresponding FVIII form containing no integrated HLEP and/or to the wild type form FVIII. The in vivo recovery can be determined in vivo in normal animals or in animal models of hemophilia A, like FVIII knockout mice, in which one would expect an increased percentage of the modified FVIII of the invention be found by antigen or activity assays in the circulation shortly (5 to 10 min.) after i.v. administration compared to the corresponding FVIII form containing no integrated HLEP and/or to the wild type form FVIII.

The in vivo recovery is preferably increased by at least 10%, more preferably by at least 20%, and even more preferably by at least 40% compared to the form without inclusion of a HLEP and/or to the wild type form of FVIII.

In yet another embodiment of the invention immunoglobulin constant regions or portions thereof are used as HLEPs. Preferably the Fc region comprised of a CH2 and CH3 domain and a hinge region of an IgG, more preferably of an IgG1 or fragments or variants thereof are used, variants including mutations which enhance binding to the neonatal Fc receptor (FcRn). The Fc region is not used to generate monomeric or dimeric Fc insertions as described in the art, but rather is inserted into the FVIII molecule such that part of the FVIII molecule is fused to its N-terminus and another part is fused to its C-terminus (FIG. 2a-n). In a preferred embodiment of the invention an unfused Fc region is coexpressed from another expression vector or even from the same expression vector which through disulfide bridge linking forms a Fc heterodimer with the Fc region within the chimeric FVIII molecule.

In addition to the extension of functional half-life of FVIII, HLEP moieties as described in this invention may also be used for insertion into other multi-domain proteins for the same purpose of half-life extension.

Therefore the invention also encompasses other modified proteins, preferably modified coagulation factors, with insertions of HLEP moieties within their amino acid sequence.

von Willebrand Factor

Von Willebrand factor (vWF) is a multimeric plasma glycoprotein with a prominent role in primary hemostasis. The mature protein consists of 2050 amino acids and is composed of homologous domains arranged in the order D'-D3-A1-A2-A3-D4-B1-B2-B3-C1-C2-CK. The amino acid sequence and the cDNA sequence of wild type vWF are disclosed in Collins et al. 1987. Proc Natl. Acad. Sci. USA 84:4393-4397. The term "von Willebrand factor" includes any mutants and variants of wild type vWF having at least 10%, preferably at least 25%, more preferably at least 50%, most preferably at least 75% of the biological activity of wild type vWF. The biological activity of wild type vWF can be determined by the man of the art using methods for ristocetin co-factor activity (Federici A B et al. 2004. Haematologica 89:77-85), binding of vWF to GP Ibα of the platelet glycoprotein complex Ib-V-IX (Sucker et al. 2006. Clin Appl Thromb Hemost. 12:305-310), or a collagen binding assay (Kailas & Talpsep. 2001. Annals of Hematology 80:466-471).

One or more HLEPs may be inserted into the vWF molecule. HLEP insertion is chosen as not to interfere with the binding capabilities of vWF to e.g. FVIII, platelets, Heparin or collagen. Suitable insertion sites include, but are not limited to, the D3-A1 junction, the D4-B1 junction, the C2-CK junction as well as A2, into which a HLEP moiety may be inserted upon partial or complete removal of the A2 domain. VWF functional activities may be assessed as described supra.

Prothrombin Factors

Prothrombin factors, including factor VII (FVII), factor IX (FIX), factor X (FX), protein C (PC), protein S, protein Z and prothrombin (PT) are a family of proteins characterized by a gla domain containing γ-carboxylated glutamic acid residues and EGF- or Kringle domains on the light chain, which is separated from the heavy chain containing the trypsin protease domain (two laminin-G domains for protein S) by a short intervening sequence which is cleaved upon activation of the protein.

The amino acid sequences and the cDNA sequences of these coagulation factors are known in the art and are disclosed for example in the PubMed protein sequence library (http://www.ncbi.nlm.nih.gov/entrez/query.fcgi?db=Protein) with accession numbers NP_000122 (FVII), NP_000124 (FIX), NP_000495 (FX), NP_000303 (PC), NP_000304 (Protein S), NP_003882 (Protein Z) and NP_000497 (Prothrombin).

Also prothrombin factors may be stabilized by the insertion of a HLEP moiety as described in this invention. Prothrombin factors include factor VII (FVII), factor IX (FIX), factor X (FX), protein C (PC), protein S, protein Z and prothrombin (PT). As described supra, prothrombin factors are characterized by a gla domain containing γ-carboxylated glutamic acid residues and EGF- or Kringle domains on the light chain, which is separated from the heavy chain containing the trypsin protease domain (two laminin-G domains for protein S) by a short intervening sequence which is cleaved upon activation of the protein. This peptide sequence is the preferred integration site for a HLEP moiety. Preferably, the HLEP is inserted such that the activation cleavage is not hampered by maintaining the natural activation sequence or by inserting artificial cleavage sites like a PACE/Furin cleavage site (Nakayama 1997. Biochem. J. 327:625-635), an artificial thrombin cleavage site (as described in WO 2004/005347) or another suitable protease cleavage site. The conservation of the activity of the respective prothrombin factor after HLEP insertion may be assessed by assays known to the man of the art. FVII activity may be determined using a commercially available chromogenic test kit (Chromogenix Coaset FVII) based on the method described by Seligsohn et al. (1978. Blood 52:978-988) and FVIIa activity can be determined using the STACLOT® FVIIa-rTF kit (Diagnostica Stago) based on the method described by Morissey et al. (1993. Blood 81:734-744). FIX activity may be assessed by a clotting assay as described by Chavin & Weidner (1984. J. Biol. Chem. 259:3387-3390). FX activity may be measured using a chromogenic assay as described by Van Wijk et al. (1981. Thromb. Res. 22:681-686). Protein C activity may be assessed by a chromogenic assay as supplied by Instrumentation Laboratory (HaemosIL Protein C) based on the method described by Comb et al. (1984. Blood 63:15-21) and protein S activity by a method described by Heeb et al. (2006. J. Thromb. Haemost. 4:385-391). Petrovan et al. (1999. Am. J. Clin. Pathol. 112:705-711 describe an activity assay for prothrombin and Tabatabai et al. (2001. Thromb. Haemost. 85:655-660) published a protein Z activity assay.

Coagulation Factor V

Coagulation factor V (FV) is a high molecular weight plasma glycoprotein that participates as a cofactor in the activation of Prothrombin by factor Xa. It is homologous to factor VIII and Ceruloplasmin and has a similar domain structure of A1-A2-B-A3-C1-C2. The amino acid sequence and the cDNA sequence of wild type FV are disclosed for example in PubMed with accession numbers NP_000121 and NM_000130, respectively.

As described above for Factor VIII, HLEP moieties could be inserted into the FV molecule for half-life extension at comparable inter-domain sites, preferably into the B domain or replacing part or all of the B domain. The FV activity can be assessed as described by Bick et al. (1973. Beitr. Pathol. 150:311-315).

Polynucleotides

The invention further relates to a polynucleotide encoding a modified coagulation factor, preferably a modified FVIII variant as described in this application. The term "polynucleotide(s)" generally refers to any polyribonucleotide or polydeoxyribonucleotide that may be unmodified RNA or DNA or modified RNA or DNA. The polynucleotide may be single- or double-stranded DNA, single or double-stranded RNA. As used herein, the term "polynucleotide(s)" also includes DNAs or RNAs that comprise one or more modified bases and/or unusual bases, such as inosine. It will be appreciated that a variety of modifications may be made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells.

The skilled person will understand that, due to the degeneracy of the genetic code, a given polypeptide can be encoded by different polynucleotides. These "variants" are encompassed by this invention.

Preferably, the polynucleotide of the invention is an isolated polynucleotide. The term "isolated" polynucleotide refers to a polynucleotide that is substantially free from other nucleic acid sequences, such as and not limited to other chromosomal and extrachromosomal DNA and RNA. Isolated polynucleotides may be purified from a host cell. Conventional nucleic acid purification methods known to skilled artisans may be used to obtain isolated polynucleotides. The term also includes recombinant polynucleotides and chemically synthesized polynucleotides.

The invention further relates to a group of polynucleotides which together encode the modified coagulation factor of the invention. A first polynucleotide in the group may encode the N-terminal part of the modified coagulation factor, and a second polynucleotide may encode the C-terminal part of the modified coagulation factor.

Yet another aspect of the invention is a plasmid or vector comprising a polynucleotide according to the invention. Preferably, the plasmid or vector is an expression vector. In a particular embodiment, the vector is a transfer vector for use in human gene therapy.

The invention also relates to a group of plasmids or vectors that comprise the above group of polynucleotides. A first plasmid or vector may contain said first polynucleotide, and a second plasmid or vector may contain said second polynucleotide. By way of example, and with reference to coagulation factor VIII, the coding sequences of the signal peptide, the A1 and A2 domains, the B domain sequence remainder and the HLEP may be cloned into the first expression vector and the coding sequences of A3, C1 and C2 with an appropriate signal peptide sequence may be cloned into the second expression vector (FIG. 2o). Both expression vectors are cotransfected into a suitable host cell, which will lead to the expression of the light and heavy chains of the FVIII molecule of the invention and the formation of a functional protein.

Alternatively, the coding sequence of the FVIII signal peptide, the A1 and A2 domains are cloned into the first expression vector and the coding sequences of the HLEP, FVIII A3, C1 and C2 with an appropriate signal peptide sequence are cloned into the second expression vector (FIG. 2p). Both expression vectors are cotransfected into a suitable host cell, which will lead to the expression of the light and heavy chains of the FVIII molecule of the invention and the formation of a functional protein.

Alternatively, both coding sequences are cloned into one expression vector either using two separate promoter sequences or one promoter and an internal ribosome entry site (IRES) element to direct the expression of both FVIII chains.

Still another aspect of the invention is a host cell comprising a polynucleotide, a plasmid or vector of the invention, or a group of polynucleotides or a group of plasmids or vectors as described herein.

The host cells of the invention may be employed in a method of producing a modified coagulation factor, preferably a modified FVIII molecule, which is part of this invention. The method comprises:
 (a) culturing host cells of the invention under conditions such that the desired insertion protein is expressed; and
 (b) optionally recovering the desired insertion protein from the host cells or from the culture medium.

It is preferred to purify the modified coagulation factors of the present invention to 80% purity, more preferably ≥95% purity, and particularly preferred is a pharmaceutically pure state that is greater than 99.9% pure with respect to contaminating macromolecules, particularly other proteins and nucleic acids, and free of infectious and pyrogenic agents. Preferably, an isolated or purified modified coagulation factor of the invention is substantially free of other, non-related polypeptides.

The various products of the invention are useful as medicaments. Accordingly, the invention relates to a pharmaceutical composition comprising a modified coagulation factor, preferably the modified FVIII molecule as described herein, a polynucleotide of the invention, or a plasmid or vector of the invention.

The invention also concerns a method of treating an individual suffering from a blood coagulation disorder such as hemophilia A or B. The method comprises administering to said individual an efficient amount of the modified coagulation factor, preferably modified FVIII or FIX as described herein. In another embodiment, the method comprises administering to the individual an efficient amount of a polynucleotide of the invention or of a plasmid or vector of the invention. Alternatively, the method may comprise administering to the individual an efficient amount of the host cells of the invention described herein.

The invention also relates to polynucleotides and their use encoding the modified VWF and Prothrombin factor variants as described above.

Expression of the Proposed Mutants

The production of recombinant mutant proteins at high levels in suitable host cells requires the assembly of the above-mentioned modified cDNAs into efficient transcriptional units together with suitable regulatory elements in a recombinant expression vector that can be propagated in various expression systems according to methods known to those skilled in the art. Efficient transcriptional regulatory elements could be derived from viruses having animal cells as their natural hosts or from the chromosomal DNA of animal cells. Preferably, promoter-enhancer combinations derived from the Simian Virus 40, adenovirus, BK polyoma virus, human cytomegalovirus, or the long terminal repeat of Rous sarcoma virus, or promoter-enhancer combinations including strongly constitutively transcribed genes in animal cells like beta-actin or GRP78 can be used. In order to achieve stable high levels of mRNA transcribed from the cDNAs, the transcriptional unit should contain in its 3'-proximal part a DNA region encoding a transcriptional termination-polyadenylation sequence. Preferably, this sequence is derived from the Simian Virus 40 early transcriptional region, the rabbit beta-globin gene, or the human tissue plasminogen activator gene.

The cDNAs are then integrated into the genome of a suitable host cell line for expression of the Factor VIII proteins. Preferably this cell line should be an animal cell-line of vertebrate origin in order to ensure correct folding, disulfide bond formation, asparagine-linked glycosylation and other post-translational modifications as well as secretion into the cultivation medium. Examples on other post-translational modifications are tyrosine O-sulfation and proteolytic processing of the nascent polypeptide chain. Examples of cell lines that can be use are monkey COS-cells, mouse L-cells, mouse C127-cells, hamster BHK-21 cells, human embryonic kidney 293 cells, and hamster CHO-cells.

The recombinant expression vector encoding the corresponding cDNAs can be introduced into an animal cell line in several different ways. For instance, recombinant expression vectors can be created from vectors based on different animal viruses. Examples of these are vectors based on baculovirus, vaccinia virus, adenovirus, and preferably bovine papilloma virus.

The transcription units encoding the corresponding DNA's can also be introduced into animal cells together with another recombinant gene which may function as a dominant selectable marker in these cells in order to facilitate the isolation of specific cell clones which have integrated the recombinant DNA into their genome. Examples of this type of dominant selectable marker genes are Tn5 amino glycoside phosphotransferase, conferring resistance to geneticin (G418), hygromycin phosphotransferase, conferring resistance to hygromycin, and puromycin acetyl transferase, conferring resistance to puromycin. The recombinant expression vector encoding such a selectable marker can reside either on the same vector as the one encoding the cDNA of the desired protein, or it can be encoded on a separate vector which is simultaneously introduced and integrated to the genome of the host cell, frequently resulting in a tight physical linkage between the different transcription units.

Other types of selectable marker genes which can be used together with the cDNA of the desired protein are based on various transcription units encoding dihydrofolate reductase (dhfr). After introduction of this type of gene into cells lacking endogenous dhfr-activity, preferentially CHO-cells (DUKX-B11, DG-44), it will enable these to grow in media lacking nucleosides. An example of such a medium is Ham's F12 without hypoxanthine, thymidin, and glycine. These dhfr-genes can be introduced together with the Factor VIII cDNA transcriptional units into CHO-cells of the above type, either linked on the same vector or on different vectors, thus creating dhfr-positive cell lines producing recombinant protein.

If the above cell lines are grown in the presence of the cytotoxic dhfr-inhibitor methotrexate, new cell lines resistant to methotrexate will emerge. These cell lines may produce recombinant protein at an increased rate due to the amplified number of linked dhfr and the desired protein's transcriptional units. When propagating these cell lines in increasing concentrations of methotrexate (1-10000 nM), new cell lines can be obtained which produce the desired protein at very high rate.

The above cell lines producing the desired protein can be grown on a large scale, either in suspension culture or on various solid supports. Examples of these supports are micro carriers based on dextran or collagen matrices, or solid supports in the form of hollow fibres or various ceramic materials. When grown in cell suspension culture or on micro carriers the culture of the above cell lines can be performed either as a bath culture or as a perfusion culture with continuous production of conditioned medium over extended periods of time. Thus, according to the present invention, the above cell lines are well suited for the development of an industrial process for the production of the desired recombinant mutant proteins Purification and Formulation The recombinant mutant protein, which accumulates in the medium of secreting cells of the above types, can be concentrated and purified by a variety of biochemical and chromatographic methods, including methods utilizing differences in size, charge, hydrophobicity, solubility, specific affinity, etc. between the desired protein and other substances in the cell cultivation medium.

An example of such purification is the adsorption of the recombinant mutant protein to a monoclonal antibody, directed to e.g. a HLEP, preferably human albumin, or directed to the respective coagulation factor, which is immobilised on a solid support. After adsorption of the FVIII mutant to the support, washing and desorption, the protein can be further purified by a variety of chromatographic techniques based on the above properties. The order of the purification steps is chosen e.g. according to capacity and selectivity of the steps, stability of the support or other aspects. Preferred purification steps e.g. are but are not limited to ion exchange chromatography steps, immune affinity chromatography steps, affinity chromatography steps, hydrophobic interaction chromatography steps, dye chromatography steps, and size exclusion chromatography steps.

In order to minimize the theoretical risk of virus contaminations, additional steps may be included in the process that allow effective inactivation or elimination of viruses. Such steps e.g. are heat treatment in the liquid or solid state, treatment with solvents and/or detergents, radiation in the visible or UV spectrum, gamma-radiation or nanofiltration.

The polynucleotides (e.g. DNA) of this invention may also be integrated into a transfer vector for use in the human gene therapy.

The various embodiments described herein may be combined with each other. The present invention will be further described in more detail in the following examples thereof. This description of specific embodiments of the invention will be made in conjunction with the appended figures.

The insertion proteins as described in this invention can be formulated into pharmaceutical preparations for therapeutic use. The purified protein may be dissolved in conventional physiologically compatible aqueous buffer solutions to which there may be added, optionally, pharmaceutical excipients to provide pharmaceutical preparations.

Such pharmaceutical carriers and excipients as well as suitable pharmaceutical formulations are well known in the art (see for example "Pharmaceutical Formulation Development of Peptides and Proteins", Frokjaer et al., Taylor & Francis (2000) or "Handbook of Pharmaceutical Excipients", 3$^{rd}$ edition, Kibbe et al., Pharmaceutical Press (2000)). In particular, the pharmaceutical composition comprising the polypeptide variant of the invention may be formulated in lyophilized or stable liquid form. The polypeptide variant may be lyophilized by a variety of procedures known in the art. Lyophilized formulations are reconstituted prior to use by the addition of one or more pharmaceutically acceptable diluents such as sterile water for injection or sterile physiological saline solution.

Formulations of the composition are delivered to the individual by any pharmaceutically suitable means of administration. Various delivery systems are known and can be used to administer the composition by any convenient route. Preferentially, the compositions of the invention are administered systemically. For systemic use, insertion proteins of the invention are formulated for parenteral (e.g. intravenous, subcutaneous, intramuscular, intraperitoneal, intracerebral, intrapulmonar, intranasal or transdermal) or enteral (e.g., oral, vaginal or rectal) delivery according to conventional methods. The most preferential routes of administration are intravenous and subcutaneous administration. The formulations can be administered continuously by infusion or by bolus injection. Some formulations encompass slow release systems.

The insertion proteins of the present invention are administered to patients in a therapeutically effective dose, meaning a dose that is sufficient to produce the desired effects, preventing or lessening the severity or spread of the condition or indication being treated without reaching a dose which produces intolerable adverse side effects. The exact dose depends on many factors as e.g. the indication, formulation, mode of administration and has to be determined in preclinical and clinical trials for each respective indication.

The pharmaceutical composition of the invention may be administered alone or in conjunction with other therapeutic agents. These agents may be incorporated as part of the same pharmaceutical. One example of such an agent is von Willebrand factor.

BRIEF DESCRIPTION OF THE DRAWINGS

FIGS. 1a-1e shows the replacement of FVIII B domain by albumin. cDNA organisation of FVIII wild-type (FVIII wt) and FVIII with the B domain replacement by albumin (FVIII-HA) are outlined. Transition sequences and the remaining amino acids of the B domain in the FVIII-HA constructs are shown. Amino acid numbering refers to the FVIII wild-type sequence as outlined in SEQ ID NO:2. The C1636S amino acid exchange in DNA pF8-1211 and the R740 deletion in pF8-1413 are indicated.

FIG. 2 schematically shows various embodiments of the cDNA encoding the modified Factor VIII polypeptides of the present invention. The HLEP may be inserted at various positions within the FVIII sequence, as described supra.

FIG. 3 shows the pharmacokinetic profile of two modified FVIII molecules with albumin integrated and partial deletion of the B-domain (DNA pF8-1211 and pF8-1413, see FIG. 1) in comparison to wild type FVIII (see example 5).

FIG. 4 shows analysis of HEK-293 cell culture supernatants at 3 time points after cell seeding, assessed for productivity if FVIII clotting activity and FVIII antigen.

EXAMPLES

Example 1

Generation of Expression Vectors for FVIII Molecules with Albumin Replacing the FVIII B Domain An expression plasmid based on pIRESpuro3 (BD Biosciences) containing the full length FVIII cDNA sequence in its multiple cloning site (pF8-FL) was first used to delete the majority of the B domain sequence and create a restriction site for insertion of foreign sequences. For that oligonucleotides We1356 and We1357 (SEQ ID NO. 5 and 6) were used in a PCR reaction using pF8-FL as a template to amplify a part of the A2 domain and the N-terminus of the B domain (fragment 1) and oligonucleotides We1358 and We1359 (SEQ ID NO. 7 and 8) were used in another PCR reaction using pF8-FL as a template to amplify the C-terminus of the B domain, the A3 domain and part of the C1 domain (fragment 2). Both fragments were gel purified. Fragment 1 was subsequently digested with restriction endonucleases PinAl and BamH1, fragment 2 was digested with restriction endonucleases PinAl and BspEl; both fragments were then purified and ligated into pF8-FL, where the BamH1/BspEl fragment encompassing part of the A2 domain, the B and A3 domains and part of the C1 domain had been removed. The resulting plasmid, pF8-DB, now basically contained a major B domain deletion with a remainder of N- and C-terminal B domain sequences joined by a PinAl site. Into this site a human albumin fragment was inserted, which had been generated by PCR amplification on albumin cDNA using primers We2502 and We2503 (SEQ ID NO. 9 and 10), PinAl digestion and purification. To remove the PinAl sites the resulting plasmid was subjected to two rounds of site-directed mutagenesis according to standard protocols (QuickChange XL Site Directed Mutagenesis Kit, Stratagene). For this oligonucleotides We2504 and We2505 (SEQ ID NO. 11 and 12) were used as mutagenic primers in the first round, and oligonucleotides We2506 and We2507 (SEQ ID NO. 13 and 14) were used in the second round of mutagenesis. The final expression plasmid was designated pF8-1210. The expression plasmid pF8-1210 encodes a FVIII molecule of 2043 amino acids in length, in which the FVIII B domain was replaced by albumin (SEQ ID NO. 4). In order to remove a free cysteine residue (amino acid 1636, SEQ ID NO. 2 and FIG. 1) site-directed mutagenesis was applied using oligonucleotides We2508 and We2509 (SEQ ID NO, 15 and 16) giving rise to plasmid pF8-1211.

Site directed mutagenesis was applied according to standard protocols (QuickChange XL Site Directed Mutagenesis Kit, Stratagene) to delete the arginine in position 740 in plasmid pF8-1211. For this oligonucleotides We2768 and We2769 (SEQ ID NO. 17 and 18) were used as mutagenic primers. The resulting expression plasmid was designated pF8-1413. A FVIII molecule where the B domain had been replaced by amino acid sequence RRGR was used as the wild-type FVIII control, the encoding plasmid was called pF8-457.

Using the protocols and plasmids described above and by applying molecular biology techniques known to those skilled in the art (and as described e.g. in Current Protocols in Molecular Biology, Ausubel F M et al. (eds.) including supplement 80, October 2007, John Wiley & Sons, Inc.; http://www.currentprotocols.com/WileyCDA/) other constructs can be made by the artisan with insertions of a HLEP molecule in positions described in FIG. 2 and linker sequences as shown exemplarily in FIGS. 1b-e.

Example 2

Generation of Expression Vectors for FVIII Molecules with an Immunoglobulin Constant Region Replacing the FVIII B Domain The insertion of an IgG Fc domain into the FVIII molecule replacing the majority of the B domain was performed in analogy to the protocols and reference described above. The resulting plasmid was called pF8-1518 and the mature protein translated from this is shown in SEQ ID NO.19.

As recycling of IgG by the neonatal Fc receptor only works with the Fc being dimeric pF8-1518 was cotransfected into HEK-293 cells with a plasmid encoding a human immunoglobulin G heavy chain region (p1335, SEQ ID No. 20). The coexpression of plasmids pF8-1518 and p1335 led to the expression of a functional FVIII molecule (table 1).

In another set of constructs FVIII heavy and light chains were expressed separately. For that pF8-1518 was mutated in that a stop codon was introduced at the very 3'-end of the IgG heavy chain sequence. The expression of such construct (pF8-1515) led to a FVIII heavy chain (A1 and A2 domain) with a few amino acids of the B domain followed by the IgG heavy chain (SEQ ID NO. 21). The FVIII light chain construct was also based on plasmid pF8-1518 in that the A1 and A2 domain coding sequences were replaced by a signal peptide. The expression of such construct (pF8-1517) led to a FVIII light chain with an IgG heavy chain attached to its N-terminus (SEQ ID NO. 22). The coexpression of plasmids pF8-1515 and pF8-1517 led to the expression of a functional FVIII molecule (table 1).

Example 3

Transfection and Expression of FVIII Mutants

Expression plasmids were grown up in *E. coli* TOP10 (Invitrogen) and purified using standard protocols (Qiagen). HEK-293 cells were transfected using the Lipofectamine 2000 reagent (Invitrogen) and grown up in serum-free medium (Invitrogen 293 Express) in the presence of 4 µg/ml Puromycin and optionally 0.5 IU/ml vWF. Transfected cell populations were spread through T-flasks into roller bottles or small scale fermenters from which supernatants were harvested for purification.

Table 1 lists expression data of a number of constructs outlined in FIGS. 1 and 2 and described in examples 1 and 2. Unless otherwise indicated, the HLEP used is albumin.

TABLE 1

| Construct | Activity [U/mL] | Antigen [U/mL] | Ratio activity/antigen |
|---|---|---|---|
| FIG. 2c | 1.0 | 7.3 | 0.14 |
| FIG. 2d | 0.4 | 4.7 | 0.09 |
| FIG. 2f | 0.44 | 1.09 | 0.40 |
| FIG. 2h | 1.04 | 0.94 | 1.11 |
| FIG. 2i | 0.33 | 0.47 | 0.70 |
| FIG. 2i (HLEP = Afamin) | 0.31 | 1.01 | 0.31 |
| FIG. 2i (HLEP = Alpha-fetoprotein) | 0.53 | 1.16 | 0.46 |
| FIG. 2o | 0.22 | 0.75 | 0.30 |
| pF8-1518 + p1335 (HLEP = Fc) | 1.19 | 1.78 | 0.67 |
| pF8-1515 + pF8-1517 (HLEP = Fc) | 1.75 | 6.68 | 0.26 |

Example 4

Purification of Factor VIII Mutants

To the expression supernatant containing the chimeric Factor VIII molecule a sufficient amount of an immune affinity resin was added to bind the FVIII activity almost completely. The immune affinity resin had been prepared by binding an appropriate anti-FVIII MAb covalently to Sephacryl S1000 resin used as a support. After washing of the resin it was filled into a chromatography column and washed again. Elution was done using a buffer containing 250 mM CaCl2 and 50% ethylene glycol.

The immune affinity chromatography (IAC) fractions containing FVIII:C activity were pooled, dialyzed against formulation buffer (excipients: sodium chloride, sucrose, histidine, calcium chloride, and Tween 80), and concentrated. Samples are either stored frozen or are freeze-dried using an appropriate freeze-drying cycle. Table 2 shows the results of a purification run using a FVIII mutant (pF8-1211 from HEK-293) and IAC as main purification step.

TABLE 2

| Sample | Volume (mL) | FVIII:C (IU/mL) | FVIII:Ag (IU/mL) | Total protein* (mg/mL) | Specific activity (IU/mg) | FVIII:C/FVIII:Ag (IU/IU) |
|---|---|---|---|---|---|---|
| Supernatant | 890 | 3.3 | 1.92 | 1.72 | 1.9 | 1.72 |
| IAC Eluate | 26 | 52.2 | 30.6 | 0.036 | 1450 | 1.71 |

*determined by measurement of Optical density (OD) at 280 nm ($OD_{280, 1\%}$ = 10.0)

Alternatively, the FVIII containing cell culture supernatant is concentrated/purified by a first ion exchange chromatography followed by further purification using immune affinity chromatography (IAC). In this case the eluate of the ion exchange chromatography is loaded onto an IAC column using the above mentioned resin.

Example 5

Analysis of Chimeric Factor VIII Activity and Antigen

For activity determination of FVIII:C in vitro either a clotting assay (e.g. Pathromtin SL reagent and FVIII deficient plasma delivered by Dade Behring, Germany) or a chromogenic assay (e.g. Coamatic FVIII:C assay delivered by Haemochrom) were used. The assays were performed according to the manufacturers instructions.

FVIII antigen (FVIII:Ag) was determined by an ELISA whose performance is known to those skilled in the art. Briefly, microplates were incubated with 100 μL per well of the capture antibody (sheep anti-human FVIII IgG, Cedarlane CL20035K-C, diluted 1:200 in Buffer A [Sigma C3041]) for 2 hours at ambient temperature. After washing plates three times with buffer B (Sigma P3563), serial dilutions of the test sample in sample diluent buffer (Cedarlane) as well as serial dilutions of a FVIII preparation (ZLB Behring; 200-2 mU/mL) in sample diluent buffer (volumes per well: 100 μL) were incubated for two hours at ambient temperature. After three wash steps with buffer B, 100 μL of a 1:2 dilution in buffer B of the detection antibody (sheep anti-human FVIII IgG, Cedarlane CL20035K-D, peroxidase labelled) were added to each well and incubated for another hour at ambient temperature. After three wash steps with buffer B, 100 μL of substrate solution (1:10 (v/v) TMB OUVF:TMB Buffer OUVG, Dade Behring) were added per well and incubated for 30 minutes at ambient temperature in the dark. Addition of 100 μL stop solution (Dade Behring, OSFA) prepared the samples for reading in a suitable microplate reader at 450 nm wavelength. Concentrations of test samples were then calculated using the standard curve with the FVIII preparation as reference.

Example 6

Pharmacokinetics of Factor VIII Mutants in Rats

The FVIII mutants were administered intravenously to narcotized CD/Lewis rats (6 rats per substance) with a dose of 100 IU/kg body weight. Blood samples were drawn at appropriate intervals starting at 5 minutes after application of the test substances. FVIII antigen content was subsequently quantified by an ELISA assay specific for human Factor VIII or by a mixed ELISA specific for albumin and FVIII, respectively (see above). The mean values of the treatment groups were used to calculate in vivo recovery after 5 min. Half-lives for each protein were calculated using the time points of the beta phase of elimination according to the formula $t_{1/2}=\ln 2/k$, whereas k is the slope of the regression line. The result is depicted in FIG. 3.

The terminal half-life calculated for the chimeric FVIII-HA constructs between 2 and 24 h was 4.97 h for 1413 and 6.86 h for 1211, the terminal half-life calculated for wild type FVIII between 2 and 8 h was 2.17 h. Therefore, a clear increase of the terminal half-life is shown for the chimeric FVIII-HA molecules extending FVIII half-life 2-3-fold.

Bioavailabilities of the chimeric FVIII-HA constructs and wild-type FVIII are shown in table 3 displaying superior bioavailabilities of the FVIII-HA proteins of the invention.

TABLE 3

Increased in vivo recovery of FVIII-HA proteins compared with FVIII wild-type (Helixate)

| | in vivo recovery [% of injected protein 5 min. after i.v. application] | increase in in vivo recovery compared to Helixate ® (wild-type FVIII) [%] |
|---|---|---|
| 1211 | 73.5 | 123.5 |
| 1413 | 87.7 | 147.8 |
| Helixate | 59.4 | |

Example 7

Functional Half-Life of a Factor VIII Mutant in Rats

The FVIII mutant pF8-1211 (expressed in HEK-293 cells and purified by IAC) as well as a control preparation (wild type FVIII Helixate NexGen) were administered intravenously to narcotized CD/Lewis rats (6 rats per substance) with a dose of 100 IU/kg body weight. Blood samples were drawn at appropriate intervals starting at 5 minutes after application of the test substances. FVIII antigen content was subsequently quantified for the control group using an ELISA assay specific for human Factor VIII (see example 4). In order to measure the FVIII:C activity of the FVIII mutant in rat plasma an assay was established determining specifically the FVIII mutant activity. In principle, the FVIII mutant was bound from the rat plasma sample to a microtiter plate via an antibody directed against human albumin and FVIII activity was then determined by a chromogenic FVIII:C assay (Coatest VIII:C/4). Briefly, 96-well microtiter plates were coated with the capture antibody (mouse anti-human albumin Mab 3E8, diluted to 5 μg/mL in carbonate/bicarbonate buffer.) over night at ambient temperature. After washing the plates with wash buffer (PBST, =phosphate buffered saline containing 0.05% Tween 20, Sigma P3563), the plates were blocked using non-fat milk in PBS (Phosphate buffered saline) and washed again with wash buffer followed by dilution buffer (50 mM Tris×HCl, 100 mM NaCl, 0.05% Tween 20 pH 7.2). Samples were applied in 40 μL volume per well and incubated for 1 h at 37° C. Washing was done using dilution buffer containing 300 mM CaCl2 followed by dilution buffer. The FVIII:C activity determination was performed using Coatest VIII:C/4 reagents.

10 μL dilution buffer and 50 μL Coatest FIXa and FX reagent were applied into the wells and incubated for 5 min at 37° C. Then, 25 μL of CaCl2 solution were added and again incubated for 10 min at 37° C. 50 μL of substrate solution was added and furthermore incubated for 10 min at 37° C. This step was followed by addition of 25 μL of stopping solution (20% acetic acid). A microtiter plate reader was used to read the absorbance at 405 nm. FVIII:C concentrations of the samples were calculated using a standard curve prepared with the FVIII mutant pF8-1211 as reference.

The FVIII:C respectively FVIII antigen results of the treatment groups were used to calculate the terminal half-lives for the corresponding proteins. The terminal functional half-life calculated for the chimeric FVIII-HSA construct pF8-1211 between 2 and 24 h was 4.44 h, the terminal half-life of FVIII antigen calculated for wild type FVIII between 2 and 8 h was 2.75 h. Therefore, a clear increase of the functional half-life of FVIII:C activity was shown for the chimeric FVIII-HSA molecule (increase by 61% compared to terminal FVIII:Ag half-life of wild type FVIII).

Example 8

In Vitro Stability of FVIII Albumin Insertion Protein

Table 4 summarizes the results of an expression study of a FVIII albumin insertion protein in serum-free cell culture.

HEK-293 cells were transfected in triplicate with pF8-1439 (FVIII albumin insertion) and pF8-457 (FVIII wild-type), respectively, seeded into T80 flasks with equal cell numbers and grown in the absence of stabilizing vWF. Culture supernatant was then harvested after 96, 120 and 144 hours and tested for FVIII activity and antigen content.

TABLE 4

| | Culture time [hrs] | FVIII antigen* [mU/mL] | SD** | FVIII activity* [mU/mL] | SD** | activity/antigen ratio |
|---|---|---|---|---|---|---|
| pF8-457 (FVIII wild type) | 96 | 679.0 | 48.9 | 1056.7 | 135.8 | 1.6 |
| pF8-1439 (FVIII albumin) | 96 | 386.7 | 44.2 | 1060.0 | 115.3 | 2.7 |
| pF8-457 (FVIII wild type) | 120 | 819.3 | 23.2 | 1720.0 | 65.6 | 2.1 |
| pF8-1439 (FVIII albumin) | 120 | 389.3 | 74.9 | 1420.0 | 196.7 | 3.6 |
| pF8-457 (FVIII wild type) | 144 | 595.7 | 59.9 | 1236.7 | 388.0 | 2.1 |
| pF8-1439 (FVIII albumin) | 144 | 381.3 | 50.1 | 1583.3 | 226.8 | 4.2 |

*mean value from triplicate experiment;
**SD, standard deviation

The results demonstrate a stabilizing effect of albumin when present as an integral part of the FVIII molecule in cell culture. The productivity is not necessarily higher in the case of the insertion protein but the specific activity of the FVIII protein (expressed in the ratio activity/antigen) is significantly higher when the albumin is an integral part of the FVIII molecule (FIG. 3) compared to wild-type FVIII.

---

The invention claimed is:

1. A modified factor VIII (FVIII) polypeptide, comprising a FVIII polypeptide having an N-terminal amino acid and a C-terminal amino acid, and a half-life enhancing polypeptide (HLEP) inserted within the B-domain between the N-terminal amino acid and the C-terminal amino acid of the FVIII polypeptide,
    wherein the FVIII polypeptide is capable of being cleaved from the HLEP moiety during activation in vivo, wherein the modified FVIII polypeptide exhibits a prolonged half-life prior to activation during a bleeding event and a half-life substantially the same as that of an unmodified FVIII peptide following activation, and
    wherein the HLEP comprises albumin or an immunoglobulin constant region polypeptide.

2. The modified FVIII polypeptide according to claim 1, wherein the modified FVIII polypeptide has a prolonged functional half-life as compared to a FVIII polypeptide lacking an inserted HLEP.

3. The modified FVIII polypeptide according to claim 1, wherein the modified FVIII polypeptide has a prolonged antigenic half-life as compared to the FVIII polypeptide lacking an inserted HLEP.

4. The modified FVIII polypeptide according to claim 2, wherein the functional half-life is increased by at least 25% as compared to the functional half-life of the FVIII polypeptide lacking an inserted HLEP.

5. The modified FVIII polypeptide according to claim 3, wherein the antigenic half-life is increased by at least 25% as compared to the antigenic half-life of the FVIII polypeptide lacking an inserted HLEP.

6. The modified FVIII polypeptide according to claim 1, wherein the modified FVIII polypeptide has an improved in vivo recovery as compared to the FVIII polypeptide lacking an inserted HLEP.

7. The modified FVIII polypeptide according to claim 6, wherein the in vivo recovery is increased by at least 10% as compared to the in vivo recovery of the FVIII polypeptide lacking an inserted HLEP.

8. The modified FVIII polypeptide according to claim 1, wherein the modified FVIII polypeptide has increased stability in serum-free culture media and/or in animal protein-free culture media as compared to the FVIII polypeptide lacking an inserted HLEP.

9. The modified FVIII polypeptide according to claim 1, wherein the B-domain of FVIII or a part thereof is replaced with the HLEP.

10. The modified FVIII polypeptide according to claim 9, wherein more than 75% of the B-domain is deleted, or more than 75% of the B-domain is replaced by linker sequences.

11. The modified FVIII polypeptide according to claim 1, wherein the modified FVIII polypeptide has at least 10% of the biological activity of the FVIII polypeptide lacking an inserted HLEP.

12. The modified FVIII polypeptide according to claim 1, wherein the half-life enhancing polypeptide is albumin.

13. The modified FVIII polypeptide according to claim 1, wherein the B-domain of FVIII has been replaced partly or completely with human albumin.

14. A pharmaceutical composition comprising a modified FVIII polypeptide according to claim 1 and a pharmaceutically acceptable carrier or excipient.

15. The modified FVIII polypeptide according to claim 1, wherein the immunoglobulin constant region polypeptide is an immunoglobulin G Fc domain.

* * * * *

UNITED STATES PATENT AND TRADEMARK OFFICE
CERTIFICATE OF CORRECTION

| | | |
|---|---|---|
| PATENT NO. | : 8,754,194 B2 | Page 1 of 1 |
| APPLICATION NO. | : 12/520840 | |
| DATED | : June 17, 2014 | |
| INVENTOR(S) | : Schulte et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 760 days.

Signed and Sealed this
Fourth Day of August, 2015

Michelle K. Lee
*Director of the United States Patent and Trademark Office*

SEQUENCE LISTING

<160> NUMBER OF SEQ ID NOS: 49

<210> SEQ ID NO 1
<211> LENGTH: 7056
<212> TYPE: DNA
<213> ORGANISM: Homo Sapiens

<400> SEQUENCE: 1

```
atgcaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtggacgc aagatttcct cctagagtgc aaaatctttt tccattcaac     180
acctcagtcg tgtacaaaaa gactctgttt gtagaattca cggatcacct tttcaacatc     240
gctaagccaa ggccaccctg gatgggtctg ctaggtccta ccatccaggc tgaggtttat     300
gatacagtgg tcattacact taagaacatg gcttcccatc ctgtcagtct tcatgctgtt     360
ggtgtatcct actggaaagc ttctgaggga gctgaatatg atgatcagac cagtcaaagg     420
gagaaagaag atgataaagt cttccctggt ggaagccata catatgtctg gcaggtcctg     480
aaagagaatg gtccaatggc ctctgaccca ctgtgcctta cctactcata tctttctcat     540
gtggacctgg taaaagactt gaattcaggc ctcattggag ccctactagt atgtagagaa     600
gggagtctgg ccaaggaaaa gacacagacc ttgcacaaat ttatactact ttttgctgta     660
tttgatgaag ggaaaagttg gcactcagaa acaaagaact ccttgatgca ggatagggat     720
gctgcatctg ctcgggcctg gcctaaaatg cacacagtca atggttatgt aaacaggtct     780
ctgccaggtc tgattggatg ccacaggaaa tcagtctatt ggcatgtgat tggaatgggc     840
accactcctg aagtgcactc aatattcctc gaaggtcaca catttcttgt gaggaaccat     900
```

```
cgccaggcgt ccttggaaat ctcgccaata actttcctta ctgctcaaac actcttgatg      960
gaccttggac agtttctact gttttgtcat atctcttccc accaacatga tggcatggaa     1020
gcttatgtca aagtagacag ctgtccagag gaaccccaac tacgaatgaa aaataatgaa     1080
gaagcggaag actatgatga tgatcttact gattctgaaa tggatgtggt caggtttgat     1140
gatgacaact ctccttcctt tatccaaatt cgctcagttg ccaagaagca tcctaaaact     1200
tgggtacatt acattgctgc tgaagaggag gactgggact atgctccctt agtcctcgcc     1260
cccgatgaca gaagttataa aagtcaatat ttgaacaatg gccctcagcg gattggtagg     1320
aagtacaaaa aagtccgatt tatggcatac acagatgaaa cctttaagac tcgtgaagct     1380
attcagcatg aatcaggaat cttgggacct ttactttatg gggaagttgg agacacactg     1440
ttgattatat ttaagaatca agcaagcaga ccatataaca tctaccctca cggaatcact     1500
gatgtccgtc ctttgtattc aaggagatta ccaaaaggtg taaaacattt gaaggatttt     1560
ccaattctgc caggagaaat attcaaatat aaatggacag tgactgtaga agatgggcca     1620
actaaatcag atcctcggtg cctgacccgc tattactcta gtttcgttaa tatggagaga     1680
gatctagctt caggactcat ggccctctc ctcatctgct acaaagaatc tgtagatcaa     1740
agaggaaacc agataatgtc agacaagagg aatgtcatcc tgttttctgt atttgatgag     1800
aaccgaagct ggtacctcac agagaatata caacgctttc tccccaatcc agctggagtg     1860
cagcttgagg atccagagtt ccaagcctcc aacatcatgc acagcatcaa tggctatgtt     1920
tttgatagtt tgcagttgtc agtttgtttg catgaggtgg catactggta cattctaagc     1980
attggagcac agactgactt cctttctgtc ttcttctctg gatataccct caaacacaaa     2040
atggtctatg aagacacact caccctattc ccattctcag agaaactgt cttcatgtcg     2100
atggaaaacc caggtctatg gattctgggg tgccacaact cagactttcg gaacagaggc     2160
atgaccgcct tactgaaggt ttctagttgt gacaagaaca ctggtgatta ttacgaggac     2220
agttatgaag atatttcagc atacttgctg agtaaaaaca atgccattga accaagaagc     2280
ttctcccaga attcaagaca ccctagcact aggcaaaagc aatttaatgc caccacaatt     2340
ccagaaaatg acatagagaa gactgaccct tggtttgcac acagaacacc tatgcctaaa     2400
atacaaaatg tctcctctag tgatttgttg atgctcttgc gacagagtcc tactccacat     2460
gggctatcct tatctgatct ccaagaagcc aaatatgaga ctttttctga tgatccatca     2520
cctggagcaa tagacagtaa taacagcctg tctgaaatga cacacttcag gccacagctc     2580
catcacagtg gggacatggt atttacccct gagtcaggcc tccaattaag attaaatgag     2640
aaactgggga caactgcagc aacagagttg aagaaacttg atttcaaagt ttctagtaca     2700
tcaaataatc tgatttcaac aattccatca gacaatttgg cagcaggtac tgataataca     2760
agttccttag acccccaag tatgccagtt cattatgata gtcaattaga taccactcta     2820
tttggcaaaa agtcatctcc ccttactgag tctggtggac ctctgagctt gagtgaagaa     2880
aataatgatt caaagttgtt agaatcaggt ttaatgaata gccaagaaag ttcatgggga     2940
aaaaatgtat cgtcaacaga gagtggtagg ttatttaaag ggaaaagagc tcatggacct     3000
gctttgttga ctaaagataa tgccttattc aaagttagca tctctttgtt aaagacaaac     3060
aaaacttcca ataattcagc aactaataga aagactcaca ttgatggccc atcattatta     3120
attgagaata gtccatcagt ctggcaaaat atattagaaa gtgacactga gtttaaaaaa     3180
gtgacacctt tgattcatga cagaatgctt atggacaaaa atgctacagc tttgaggcta     3240
aatcatatgt caaataaaac tacttcatca aaaaacatgg aaatggtcca acagaaaaaa     3300
```

```
gagggcccca ttccaccaga tgcacaaaat ccagatatgt cgttctttaa gatgctattc   3360
ttgccagaat cagcaaggtg gatacaaagg actcatggaa agaactctct gaactctggg   3420
caaggcccca gtccaaagca attagtatcc ttaggaccag aaaaatctgt ggaaggtcag   3480
aatttcttgt ctgagaaaaa caaagtggta gtaggaaagg gtgaatttac aaaggacgta   3540
ggactcaaag agatggtttt tccaagcagc agaaacctat ttcttactaa cttggataat   3600
ttacatgaaa ataatacaca caatcaagaa aaaaaattc aggaagaaat agaaagaag   3660 gaaacattaa tccaagagaa tgtagttttg cctcagatac atacagtgac tggcactaag   3720
aatttcatga agaaccttt cttactgagc actaggcaaa atgtagaagg ttcatatgac   3780
ggggcatatg ctccagtact tcaagatttt aggtcattaa atgattcaac aaatagaaca   3840
aagaaacaca cagctcattt ctcaaaaaaa ggggaggaag aaaacttgga aggcttggga   3900
aatcaaacca agcaaattgt agagaaatat gcatgcacca caaggatatc tcctaataca   3960
agccagcaga attttgtcac gcaacgtagt aagagagctt tgaaacaatt cagactccca   4020
ctagaagaaa cagaacttga aaaaggata attgtggatg cacctcaac ccagtggtcc   4080 aaaaacatga acatttgac cccgagcacc ctcacacaga tagactacaa tgagaaggag   4140
aaaggggcca ttactcagtc tcccttatca gattgcctta cgaggagtca tagcatccct   4200
caagcaaata gatctccatt acccattgca aaggtatcat catttccatc tattagacct   4260
atatatctga ccagggtcct attccaagac aactcttctc atcttccagc agcatcttat   4320
agaaagaaag attctggggt ccaagaaagc agtcatttct tacaaggagc caaaaaaat   4380 aacctttctt tagccattct aaccttggag atgactggtg atcaaagaga ggttggctcc   4440
ctggggacaa gtgccacaaa ttcagtcaca tacaagaaag ttgagaacac tgttctcccg   4500
aaaccagact tgcccaaaac atctggcaaa gttgaattgc ttccaaaagt tcacatttat   4560
cagaaggacc tattccctac ggaaactagc aatgggtctc ctggccatct ggatctcgtg   4620
gaagggagcc ttcttcaggg aacagaggga gcgattaagt ggaatgaagc aaacagacct   4680
ggaaaagttc cctttctgag agtagcaaca gaaagctctg caaagactcc ctccaagcta   4740
ttggatcctc ttgcttggga taaccactat ggtactcaga taccaaaaga agagtggaaa   4800
tcccaagaga agtcaccaga aaaaacagct tttaagaaaa aggataccat tttgtccctg   4860
aacgcttgtg aaagcaatca tgcaatagca gcaataaatg agggacaaaa taagcccgaa   4920
atagaagtca cctgggcaaa gcaaggtagg actgaaaggc tgtgctctca aaacccacca   4980
gtcttgaaac gccatcaacg ggaaataact cgtactactc ttcagtcaga tcaagaggaa   5040
attgactatg atgataccat atcagttgaa atgaagaagg aagattttga catttatgat   5100
gaggatgaaa atcagagccc ccgcagcttt caaaagaaaa cacgcactta ttttattgct   5160
gcagtggaga ggctctggga ttatgggatg agtagctccc cacatgttct aagaaacagg   5220
gctcagagtg gcagtgtccc tcagttcaag aaagttgttt ccaggaatt tactgatggc   5280 tcctttactc agcccttata ccgtggagaa ctaaatgaac atttgggact cctggggcca   5340
tatataagag cagaagttga agataatatc atggtaactt tcagaaatca ggcctctcgt   5400
ccctattcct tctattctag ccttatttct tatgaggaag atcagaggca aggagcagaa   5460
cctagaaaaa actttgtcaa gcctaatgaa accaaaactt acttttggaa agtgcaacat   5520
catatggcac ccactaaaga tgagtttgac tgcaaagcct gggcttattt ctctgatgtt   5580
gacctggaaa aagatgtgca ctcaggcctg attggacccc ttctggtctg ccacactaac   5640
acactgaacc ctgctcatgg gagacaagtg acagtacagg aatttgctct gttttcacc   5700
```

-continued

```
atctttgatg agaccaaaag ctggtacttc actgaaaata tggaaagaaa ctgcagggct      5760
ccctgcaata tccagatgga agatcccact tttaaagaga attatcgctt ccatgcaatc      5820
aatggctaca taatggatac actacctggc ttagtaatgg ctcaggatca aaggattcga      5880
tggtatctgc tcagcatggg cagcaatgaa acatccatt ctattcattt cagtggacat       5940
gtgttcactg tacgaaaaaa agaggagtat aaaatggcac tgtacaatct ctatccaggt      6000 gttttttgaga cagtggaaat gttaccatcc aaagctggaa tttggcgggt ggaatgcctt     6060
attggcgagc atctacatgc tgggatgagc acacttttc tggtgtacag caataagtgt      6120
cagactcccc tggaatggc ttctggacac attagagatt ttcagattac agcttcagga      6180
caatatggac agtgggcccc aaagctggcc agacttcatt attccggatc aatcaatgcc     6240
tggagcacca aggagccctt tcttggatc aaggtggatc tgttggcacc aatgattatt       6300
cacggcatca agacccaggg tgcccgtcag aagttctcca gcctctacat ctctcagttt      6360
atcatcatgt atagtcttga tgggaagaag tggcagactt atcgaggaaa ttccactgga      6420
accttaatgg tcttctttgg caatgtggat tcatctggga taaaacacaa tatttttaac     6480
cctccaatta ttgctcgata catccgtttg cacccaactc attatagcat tcgcagcact     6540
cttcgcatgg agttgatggg ctgtgattta aatagttgca gcatgccatt gggaatggag    6600
agtaaagcaa tatcagatgc acagattact gcttcatcct actttaccaa tatgtttgcc     6660
acctggtctc cttcaaaagc tcgacttcac ctccaaggga ggagtaatgc ctggagacct    6720
caggtgaata atccaaaaga gtggctgcaa gtggacttcc agaagacaat gaaagtcaca     6780
ggagtaacta ctcagggagt aaaatctctg cttaccagca tgtatgtgaa ggagttcctc      6840
atctccagca gtcaagatgg ccatcagtgg actctctttt ttcagaatgg caaagtaaag    6900
gtttttcagg gaaatcaaga ctccttcaca cctgtggtga actctctaga cccaccgtta     6960
ctgactcgct accttcgaat tcaccccag agttgggtgc accagattgc cctgaggatg     7020
gaggttctgg gctgcgaggc acaggacctc tactga                               7056
```

<210> SEQ ID NO 2
<211> LENGTH: 2332
<212> TYPE: PRT
<213> ORGANISM: Homo Sapiens

<400> SEQUENCE: 2

```
Ala Thr Arg Arg Tyr Tyr Leu Gly Ala Val Glu Leu Ser Trp Asp Tyr
  1               5                  10                  15

Met Gln Ser Asp Leu Gly Glu Leu Pro Val Asp Ala Arg Phe Pro Pro
             20                  25                  30

Arg Val Pro Lys Ser Phe Pro Phe Asn Thr Ser Val Val Tyr Lys Lys
         35                  40                  45

Thr Leu Phe Val Glu Phe Thr Asp His Leu Phe Asn Ile Ala Lys Pro
     50                  55                  60

Arg Pro Pro Trp Met Gly Leu Leu Gly Pro Thr Ile Gln Ala Glu Val
 65                  70                  75                  80

Tyr Asp Thr Val Val Ile Thr Leu Lys Asn Met Ala Ser His Pro Val
                 85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140
```

-continued

```
Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
            165                 170                 175

Leu Val Cys Arg Glu Gly Ser Leu Ala Lys Glu Lys Thr Gln Thr Leu
        180                 185                 190

His Lys Phe Ile Leu Leu Phe Ala Val Phe Asp Glu Gly Lys Ser Trp
    195                 200                 205

His Ser Glu Thr Lys Asn Ser Leu Met Gln Asp Arg Asp Ala Ala Ser
210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
            245                 250                 255

Val Ile Gly Met Gly Thr Thr Pro Glu Val His Ser Ile Phe Leu Glu
        260                 265                 270

Gly His Thr Phe Leu Val Arg Asn His Arg Gln Ala Ser Leu Glu Ile
    275                 280                 285

Ser Pro Ile Thr Phe Leu Thr Ala Gln Thr Leu Leu Met Asp Leu Gly
290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
            325                 330                 335

Met Lys Asn Asn Glu Glu Ala Glu Asp Tyr Asp Asp Asp Leu Thr Asp
        340                 345                 350

Ser Glu Met Asp Val Val Arg Phe Asp Asp Asp Asn Ser Pro Ser Phe
    355                 360                 365

Ile Gln Ile Arg Ser Val Ala Lys Lys His Pro Lys Thr Trp Val His
370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
            405                 410                 415

Gln Arg Ile Gly Arg Lys Tyr Lys Lys Val Arg Phe Met Ala Tyr Thr
        420                 425                 430

Asp Glu Thr Phe Lys Thr Arg Glu Ala Ile Gln His Glu Ser Gly Ile
    435                 440                 445

Leu Gly Pro Leu Leu Tyr Gly Glu Val Gly Asp Thr Leu Leu Ile Ile
450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
            485                 490                 495

His Leu Lys Asp Phe Pro Ile Leu Pro Gly Glu Ile Phe Lys Tyr Lys
        500                 505                 510

Trp Thr Val Thr Val Glu Asp Gly Pro Thr Lys Ser Asp Pro Arg Cys
    515                 520                 525

Leu Thr Arg Tyr Tyr Ser Ser Phe Val Asn Met Glu Arg Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
```

```
                    565                 570                 575
Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
                595                 600                 605

Gln Ala Ser Asn Ile Met His Ser Ile Asn Gly Tyr Val Phe Asp Ser
                610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
                675                 680                 685

Ile Leu Gly Cys His Asn Ser Asp Phe Arg Asn Arg Gly Met Thr Ala
                690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Arg Ser Thr Arg
                740                 745                 750

Gln Lys Gln Phe Asn Ala Thr Thr Ile Pro Glu Asn Asp Ile Glu Lys
                755                 760                 765

Thr Asp Pro Trp Phe Ala His Arg Thr Pro Met Pro Lys Ile Gln Asn
                770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
                820                 825                 830

Glu Met Thr His Phe Arg Pro Gln Leu His His Ser Gly Asp Met Val
                835                 840                 845

Phe Thr Pro Glu Ser Gly Leu Gln Leu Arg Leu Asn Glu Lys Leu Gly
                850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
                900                 905                 910

Tyr Asp Ser Gln Leu Asp Thr Thr Leu Phe Gly Lys Lys Ser Ser Pro
                915                 920                 925

Leu Thr Glu Ser Gly Gly Pro Leu Ser Leu Ser Glu Glu Asn Asn Asp
                930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
                980                 985                 990
```

```
Val Ser Ile Ser Leu Leu Lys Thr Asn Lys Thr Ser Asn Asn Ser Ala
    995                 1000                1005

Thr Asn Arg Lys Thr His Ile Asp Gly Pro Ser Leu Leu Ile Glu
1010                1015                1020

Asn Ser Pro Ser Val Trp Gln Asn Ile Leu Glu Ser Asp Thr Glu
1025                1030                1035

Phe Lys Lys Val Thr Pro Leu Ile His Asp Arg Met Leu Met Asp
1040                1045                1050

Lys Asn Ala Thr Ala Leu Arg Leu Asn His Met Ser Asn Lys Thr
1055                1060                1065

Thr Ser Ser Lys Asn Met Glu Met Val Gln Gln Lys Lys Glu Gly
1070                1075                1080

Pro Ile Pro Pro Asp Ala Gln Asn Pro Asp Met Ser Phe Phe Lys
1085                1090                1095

Met Leu Phe Leu Pro Glu Ser Ala Arg Trp Ile Gln Arg Thr His
1100                1105                1110

Gly Lys Asn Ser Leu Asn Ser Gly Gln Gly Pro Ser Pro Lys Gln
1115                1120                1125

Leu Val Ser Leu Gly Pro Glu Lys Ser Val Glu Gly Gln Asn Phe
1130                1135                1140

Leu Ser Glu Lys Asn Lys Val Val Val Gly Lys Gly Glu Phe Thr
1145                1150                1155

Lys Asp Val Gly Leu Lys Glu Met Val Phe Pro Ser Ser Arg Asn
1160                1165                1170

Leu Phe Leu Thr Asn Leu Asp Asn Leu His Glu Asn Asn Thr His
1175                1180                1185

Asn Gln Glu Lys Lys Ile Gln Glu Glu Ile Glu Lys Lys Glu Thr
1190                1195                1200

Leu Ile Gln Glu Asn Val Val Leu Pro Gln Ile His Thr Val Thr
1205                1210                1215

Gly Thr Lys Asn Phe Met Lys Asn Leu Phe Leu Leu Ser Thr Arg
1220                1225                1230

Gln Asn Val Glu Gly Ser Tyr Asp Gly Ala Tyr Ala Pro Val Leu
1235                1240                1245

Gln Asp Phe Arg Ser Leu Asn Asp Ser Thr Asn Arg Thr Lys Lys
1250                1255                1260

His Thr Ala His Phe Ser Lys Lys Gly Glu Glu Glu Asn Leu Glu
1265                1270                1275

Gly Leu Gly Asn Gln Thr Lys Gln Ile Val Glu Lys Tyr Ala Cys
1280                1285                1290

Thr Thr Arg Ile Ser Pro Asn Thr Ser Gln Gln Asn Phe Val Thr
1295                1300                1305

Gln Arg Ser Lys Arg Ala Leu Lys Gln Phe Arg Leu Pro Leu Glu
1310                1315                1320

Glu Thr Glu Leu Glu Lys Arg Ile Ile Val Asp Asp Thr Ser Thr
1325                1330                1335

Gln Trp Ser Lys Asn Met Lys His Leu Thr Pro Ser Thr Leu Thr
1340                1345                1350

Gln Ile Asp Tyr Asn Glu Lys Glu Lys Gly Ala Ile Thr Gln Ser
1355                1360                1365

Pro Leu Ser Asp Cys Leu Thr Arg Ser His Ser Ile Pro Gln Ala
1370                1375                1380

Asn Arg Ser Pro Leu Pro Ile Ala Lys Val Ser Ser Phe Pro Ser
1385                1390                1395
```

-continued

```
Ile Arg Pro Ile Tyr Leu Thr Arg Val Leu Phe Gln Asp Asn Ser
    1400                1405                1410
Ser His Leu Pro Ala Ala Ser Tyr Arg Lys Lys Asp Ser Gly Val
    1415                1420                1425
Gln Glu Ser Ser His Phe Leu Gln Gly Ala Lys Lys Asn Asn Leu
    1430                1435                1440
Ser Leu Ala Ile Leu Thr Leu Glu Met Thr Gly Asp Gln Arg Glu
    1445                1450                1455
Val Gly Ser Leu Gly Thr Ser Ala Thr Asn Ser Val Thr Tyr Lys
    1460                1465                1470
Lys Val Glu Asn Thr Val Leu Pro Lys Pro Asp Leu Pro Lys Thr
    1475                1480                1485
Ser Gly Lys Val Glu Leu Leu Pro Lys Val His Ile Tyr Gln Lys
    1490                1495                1500
Asp Leu Phe Pro Thr Glu Thr Ser Asn Gly Ser Pro Gly His Leu
    1505                1510                1515
Asp Leu Val Glu Gly Ser Leu Leu Gln Gly Thr Glu Gly Ala Ile
    1520                1525                1530
Lys Trp Asn Glu Ala Asn Arg Pro Gly Lys Val Pro Phe Leu Arg
    1535                1540                1545
Val Ala Thr Glu Ser Ser Ala Lys Thr Pro Ser Lys Leu Leu Asp
    1550                1555                1560
Pro Leu Ala Trp Asp Asn His Tyr Gly Thr Gln Ile Pro Lys Glu
    1565                1570                1575
Glu Trp Lys Ser Gln Glu Lys Ser Pro Glu Lys Thr Ala Phe Lys
    1580                1585                1590
Lys Lys Asp Thr Ile Leu Ser Leu Asn Ala Cys Glu Ser Asn His
    1595                1600                1605
Ala Ile Ala Ala Ile Asn Glu Gly Gln Asn Lys Pro Glu Ile Glu
    1610                1615                1620
Val Thr Trp Ala Lys Gln Gly Arg Thr Glu Arg Leu Cys Ser Gln
    1625                1630                1635
Asn Pro Pro Val Leu Lys Arg His Gln Arg Glu Ile Thr Arg Thr
    1640                1645                1650
Thr Leu Gln Ser Asp Gln Glu Glu Ile Asp Tyr Asp Asp Thr Ile
    1655                1660                1665
Ser Val Glu Met Lys Lys Glu Asp Phe Asp Ile Tyr Asp Glu Asp
    1670                1675                1680
Glu Asn Gln Ser Pro Arg Ser Phe Gln Lys Lys Thr Arg His Tyr
    1685                1690                1695
Phe Ile Ala Ala Val Glu Arg Leu Trp Asp Tyr Gly Met Ser Ser
    1700                1705                1710
Ser Pro His Val Leu Arg Asn Arg Ala Gln Ser Gly Ser Val Pro
    1715                1720                1725
Gln Phe Lys Lys Val Val Phe Gln Glu Phe Thr Asp Gly Ser Phe
    1730                1735                1740
Thr Gln Pro Leu Tyr Arg Gly Glu Leu Asn Glu His Leu Gly Leu
    1745                1750                1755
Leu Gly Pro Tyr Ile Arg Ala Glu Val Glu Asp Asn Ile Met Val
    1760                1765                1770
Thr Phe Arg Asn Gln Ala Ser Arg Pro Tyr Ser Phe Tyr Ser Ser
    1775                1780                1785
Leu Ile Ser Tyr Glu Glu Asp Gln Arg Gln Gly Ala Glu Pro Arg
```

```
                1790              1795              1800

Lys Asn Phe Val Lys Pro Asn Glu Thr Lys Thr Tyr Phe Trp Lys
    1805              1810              1815

Val Gln His His Met Ala Pro Thr Lys Asp Glu Phe Asp Cys Lys
    1820              1825              1830

Ala Trp Ala Tyr Phe Ser Asp Val Asp Leu Glu Lys Asp Val His
    1835              1840              1845

Ser Gly Leu Ile Gly Pro Leu Leu Val Cys His Thr Asn Thr Leu
    1850              1855              1860

Asn Pro Ala His Gly Arg Gln Val Thr Val Gln Glu Phe Ala Leu
    1865              1870              1875

Phe Phe Thr Ile Phe Asp Glu Thr Lys Ser Trp Tyr Phe Thr Glu
    1880              1885              1890

Asn Met Glu Arg Asn Cys Arg Ala Pro Cys Asn Ile Gln Met Glu
    1895              1900              1905

Asp Pro Thr Phe Lys Glu Asn Tyr Arg Phe His Ala Ile Asn Gly
    1910              1915              1920

Tyr Ile Met Asp Thr Leu Pro Gly Leu Val Met Ala Gln Asp Gln
    1925              1930              1935

Arg Ile Arg Trp Tyr Leu Leu Ser Met Gly Ser Asn Glu Asn Ile
    1940              1945              1950

His Ser Ile His Phe Ser Gly His Val Phe Thr Val Arg Lys Lys
    1955              1960              1965

Glu Glu Tyr Lys Met Ala Leu Tyr Asn Leu Tyr Pro Gly Val Phe
    1970              1975              1980

Glu Thr Val Glu Met Leu Pro Ser Lys Ala Gly Ile Trp Arg Val
    1985              1990              1995

Glu Cys Leu Ile Gly Glu His Leu His Ala Gly Met Ser Thr Leu
    2000              2005              2010

Phe Leu Val Tyr Ser Asn Lys Cys Gln Thr Pro Leu Gly Met Ala
    2015              2020              2025

Ser Gly His Ile Arg Asp Phe Gln Ile Thr Ala Ser Gly Gln Tyr
    2030              2035              2040

Gly Gln Trp Ala Pro Lys Leu Ala Arg Leu His Tyr Ser Gly Ser
    2045              2050              2055

Ile Asn Ala Trp Ser Thr Lys Glu Pro Phe Ser Trp Ile Lys Val
    2060              2065              2070

Asp Leu Leu Ala Pro Met Ile Ile His Gly Ile Lys Thr Gln Gly
    2075              2080              2085

Ala Arg Gln Lys Phe Ser Ser Leu Tyr Ile Ser Gln Phe Ile Ile
    2090              2095              2100

Met Tyr Ser Leu Asp Gly Lys Lys Trp Gln Thr Tyr Arg Gly Asn
    2105              2110              2115

Ser Thr Gly Thr Leu Met Val Phe Phe Gly Asn Val Asp Ser Ser
    2120              2125              2130

Gly Ile Lys His Asn Ile Phe Asn Pro Pro Ile Ile Ala Arg Tyr
    2135              2140              2145

Ile Arg Leu His Pro Thr His Tyr Ser Ile Arg Ser Thr Leu Arg
    2150              2155              2160

Met Glu Leu Met Gly Cys Asp Leu Asn Ser Cys Ser Met Pro Leu
    2165              2170              2175

Gly Met Glu Ser Lys Ala Ile Ser Asp Ala Gln Ile Thr Ala Ser
    2180              2185              2190
```

-continued

```
Ser Tyr Phe Thr Asn Met Phe Ala Thr Trp Ser Pro Ser Lys Ala
2195                2200                2205

Arg Leu His Leu Gln Gly Arg Ser Asn Ala Trp Arg Pro Gln Val
2210                2215                2220

Asn Asn Pro Lys Glu Trp Leu Gln Val Asp Phe Gln Lys Thr Met
2225                2230                2235

Lys Val Thr Gly Val Thr Thr Gln Gly Val Lys Ser Leu Leu Thr
2240                2245                2250

Ser Met Tyr Val Lys Glu Phe Leu Ile Ser Ser Ser Gln Asp Gly
2255                2260                2265

His Gln Trp Thr Leu Phe Phe Gln Asn Gly Lys Val Lys Val Phe
2270                2275                2280

Gln Gly Asn Gln Asp Ser Phe Thr Pro Val Val Asn Ser Leu Asp
2285                2290                2295

Pro Pro Leu Leu Thr Arg Tyr Leu Arg Ile His Pro Gln Ser Trp
2300                2305                2310

Val His Gln Ile Ala Leu Arg Met Glu Val Leu Gly Cys Glu Ala
2315                2320                2325

Gln Asp Leu Tyr
2330

<210> SEQ ID NO 3
<211> LENGTH: 585
<212> TYPE: PRT
<213> ORGANISM: Homo Sapiens

<400> SEQUENCE: 3

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220
```

```
Lys Ala Glu Phe Ala Glu Val Ser Lys Leu Val Thr Asp Leu Thr Lys
225                 230                 235                 240

Val His Thr Glu Cys His Gly Asp Leu Leu Glu Cys Ala Asp Asp
            245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 4
<211> LENGTH: 2043
<212> TYPE: PRT
<213> ORGANISM: Artificial
<220> FEATURE:
<223> OTHER INFORMATION: Amino acid sequence of mature human FVIII with
      B domain replacement by human albumin

<400> SEQUENCE: 4
```

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
            115                 120                 125

Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
        290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
            355                 360                 365

Ile Gln Ile Arg Ser Val Ala Lys Lys His Pro Lys Thr Trp Val His
        370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430
```

-continued

Asp Glu Thr Phe Lys Thr Arg Glu Ala Ile Gln His Glu Ser Gly Ile
              435                 440                 445

Leu Gly Pro Leu Leu Tyr Gly Glu Val Gly Asp Thr Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
    595                 600                 605

Gln Ala Ser Asn Ile Met His Ser Ile Asn Gly Tyr Val Phe Asp Ser
            610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
    675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Arg Ser Thr Arg
            740                 745                 750

Gln Lys Gln Asp Ala His Lys Ser Glu Val Ala His Arg Phe Lys Asp
            755                 760                 765

Leu Gly Glu Glu Asn Phe Lys Ala Leu Val Leu Ile Ala Phe Ala Gln
    770                 775                 780

Tyr Leu Gln Gln Cys Pro Phe Glu Asp His Val Lys Leu Val Asn Glu
785                 790                 795                 800

Val Thr Glu Phe Ala Lys Thr Cys Val Ala Asp Glu Ser Ala Glu Asn
                805                 810                 815

Cys Asp Lys Ser Leu His Thr Leu Phe Gly Asp Lys Leu Cys Thr Val
            820                 825                 830

Ala Thr Leu Arg Glu Thr Tyr Gly Glu Met Ala Asp Cys Cys Ala Lys
    835                 840                 845

Gln Glu Pro Glu Arg Asn Glu Cys Phe Leu Gln His Lys Asp Asp Asn

-continued

```
             850                 855                 860
Pro Asn Leu Pro Arg Leu Val Arg Pro Glu Val Asp Val Met Cys Thr
865                 870                 875                 880

Ala Phe His Asp Asn Glu Glu Thr Phe Leu Lys Lys Tyr Leu Tyr Glu
                885                 890                 895

Ile Ala Arg Arg His Pro Tyr Phe Tyr Ala Pro Glu Leu Leu Phe Phe
                900                 905                 910

Ala Lys Arg Tyr Lys Ala Ala Phe Thr Glu Cys Cys Gln Ala Ala Asp
                915                 920                 925

Lys Ala Ala Cys Leu Leu Pro Lys Leu Asp Glu Leu Arg Asp Glu Gly
930                 935                 940

Lys Ala Ser Ser Ala Lys Gln Arg Leu Lys Cys Ala Ser Leu Gln Lys
945                 950                 955                 960

Phe Gly Glu Arg Ala Phe Lys Ala Trp Ala Val Ala Arg Leu Ser Gln
                965                 970                 975

Arg Phe Pro Lys Ala Glu Phe Ala Glu Val Ser Lys Leu Val Thr Asp
                980                 985                 990

Leu Thr Lys Val His Thr Glu Cys  Cys His Gly Asp Leu Leu Glu Cys
                995                 1000                1005

Ala Asp  Asp Arg Ala Asp Leu  Ala Lys Tyr Ile Cys  Glu Asn Gln
1010                 1015                1020

Asp Ser  Ile Ser Ser Lys Leu  Lys Glu Cys Cys Glu  Lys Pro Leu
1025                 1030                1035

Leu Glu  Lys Ser His Cys Ile  Ala Glu Val Glu Asn  Asp Glu Met
1040                 1045                1050

Pro Ala  Asp Leu Pro Ser Leu  Ala Ala Asp Phe Val  Glu Ser Lys
1055                 1060                1065

Asp Val  Cys Lys Asn Tyr Ala  Glu Ala Lys Asp Val  Phe Leu Gly
1070                 1075                1080

Met Phe  Leu Tyr Glu Tyr Ala  Arg Arg His Pro Asp  Tyr Ser Val
1085                 1090                1095

Val Leu  Leu Leu Arg Leu Ala  Lys Thr Tyr Glu Thr  Thr Leu Glu
1100                 1105                1110

Lys Cys  Cys Ala Ala Ala Asp  Pro His Glu Cys Tyr  Ala Lys Val
1115                 1120                1125

Phe Asp  Glu Phe Lys Pro Leu  Val Glu Glu Pro Gln  Asn Leu Ile
1130                 1135                1140

Lys Gln  Asn Cys Glu Leu Phe  Glu Gln Leu Gly Glu  Tyr Lys Phe
1145                 1150                1155

Gln Asn  Ala Leu Leu Val Arg  Tyr Thr Lys Lys Val  Pro Gln Val
1160                 1165                1170

Ser Thr  Pro Thr Leu Val Glu  Val Ser Arg Asn Leu  Gly Lys Val
1175                 1180                1185

Gly Ser  Lys Cys Cys Lys His  Pro Glu Ala Lys Arg  Met Pro Cys
1190                 1195                1200

Ala Glu  Asp Tyr Leu Ser Val  Val Leu Asn Gln Leu  Cys Val Leu
1205                 1210                1215

His Glu  Lys Thr Pro Val Ser  Asp Arg Val Thr Lys  Cys Cys Thr
1220                 1225                1230

Glu Ser  Leu Val Asn Arg Arg  Pro Cys Phe Ser Ala  Leu Glu Val
1235                 1240                1245

Asp Glu  Thr Tyr Val Pro Lys  Glu Phe Asn Ala Glu  Thr Phe Thr
1250                 1255                1260
```

-continued

| | | | | | | | | | | | | | | |
|---|---|---|---|---|---|---|---|---|---|---|---|---|---|---|
|Phe|His|Ala|Asp|Ile|Cys|Thr|Leu|Ser|Glu|Lys|Glu|Arg|Gln|Ile|
| |1265| | | |1270| | | |1275| | | | | |

Lys Lys Gln Thr Ala Leu Val Glu Leu Val Lys His Lys Pro Lys
1280                1285                1290

Ala Thr Lys Glu Gln Leu Lys Ala Val Met Asp Asp Phe Ala Ala
1295                1300                1305

Phe Val Glu Lys Cys Cys Lys Ala Asp Asp Lys Glu Thr Cys Phe
1310                1315                1320

Ala Glu Glu Gly Lys Lys Leu Val Ala Ala Ser Gln Ala Ala Leu
1325                1330                1335

Gly Leu Gly Arg Thr Glu Arg Leu Cys Ser Gln Asn Pro Pro Val
1340                1345                1350

Leu Lys Arg His Gln Arg Glu Ile Thr Arg Thr Thr Leu Gln Ser
1355                1360                1365

Asp Gln Glu Glu Ile Asp Tyr Asp Asp Thr Ile Ser Val Glu Met
1370                1375                1380

Lys Lys Glu Asp Phe Asp Ile Tyr Asp Glu Asp Glu Asn Gln Ser
1385                1390                1395

Pro Arg Ser Phe Gln Lys Lys Thr Arg His Tyr Phe Ile Ala Ala
1400                1405                1410

Val Glu Arg Leu Trp Asp Tyr Gly Met Ser Ser Ser Pro His Val
1415                1420                1425

Leu Arg Asn Arg Ala Gln Ser Gly Ser Val Pro Gln Phe Lys Lys
1430                1435                1440

Val Val Phe Gln Glu Phe Thr Asp Gly Ser Phe Thr Gln Pro Leu
1445                1450                1455

Tyr Arg Gly Glu Leu Asn Glu His Leu Gly Leu Leu Gly Pro Tyr
1460                1465                1470

Ile Arg Ala Glu Val Glu Asp Asn Ile Met Val Thr Phe Arg Asn
1475                1480                1485

Gln Ala Ser Arg Pro Tyr Ser Phe Tyr Ser Ser Leu Ile Ser Tyr
1490                1495                1500

Glu Glu Asp Gln Arg Gln Gly Ala Glu Pro Arg Lys Asn Phe Val
1505                1510                1515

Lys Pro Asn Glu Thr Lys Thr Tyr Phe Trp Lys Val Gln His His
1520                1525                1530

Met Ala Pro Thr Lys Asp Glu Phe Asp Cys Lys Ala Trp Ala Tyr
1535                1540                1545

Phe Ser Asp Val Asp Leu Glu Lys Asp Val His Ser Gly Leu Ile
1550                1555                1560

Gly Pro Leu Leu Val Cys His Thr Asn Thr Leu Asn Pro Ala His
1565                1570                1575

Gly Arg Gln Val Thr Val Gln Glu Phe Ala Leu Phe Phe Thr Ile
1580                1585                1590

Phe Asp Glu Thr Lys Ser Trp Tyr Phe Thr Glu Asn Met Glu Arg
1595                1600                1605

Asn Cys Arg Ala Pro Cys Asn Ile Gln Met Glu Asp Pro Thr Phe
1610                1615                1620

Lys Glu Asn Tyr Arg Phe His Ala Ile Asn Gly Tyr Ile Met Asp
1625                1630                1635

Thr Leu Pro Gly Leu Val Met Ala Gln Asp Gln Arg Ile Arg Trp
1640                1645                1650

Tyr Leu Leu Ser Met Gly Ser Asn Glu Asn Ile His Ser Ile His
1655                1660                1665

Phe Ser Gly His Val Phe Thr Val Arg Lys Lys Glu Glu Tyr Lys
1670                1675                1680

Met Ala Leu Tyr Asn Leu Tyr Pro Gly Val Phe Glu Thr Val Glu
1685                1690                1695

Met Leu Pro Ser Lys Ala Gly Ile Trp Arg Val Glu Cys Leu Ile
1700                1705                1710

Gly Glu His Leu His Ala Gly Met Ser Thr Leu Phe Leu Val Tyr
1715                1720                1725

Ser Asn Lys Cys Gln Thr Pro Leu Gly Met Ala Ser Gly His Ile
1730                1735                1740

Arg Asp Phe Gln Ile Thr Ala Ser Gly Gln Tyr Gly Gln Trp Ala
1745                1750                1755

Pro Lys Leu Ala Arg Leu His Tyr Ser Gly Ser Ile Asn Ala Trp
1760                1765                1770

Ser Thr Lys Glu Pro Phe Ser Trp Ile Lys Val Asp Leu Leu Ala
1775                1780                1785

Pro Met Ile Ile His Gly Ile Lys Thr Gln Gly Ala Arg Gln Lys
1790                1795                1800

Phe Ser Ser Leu Tyr Ile Ser Gln Phe Ile Ile Met Tyr Ser Leu
1805                1810                1815

Asp Gly Lys Lys Trp Gln Thr Tyr Arg Gly Asn Ser Thr Gly Thr
1820                1825                1830

Leu Met Val Phe Phe Gly Asn Val Asp Ser Ser Gly Ile Lys His
1835                1840                1845

Asn Ile Phe Asn Pro Pro Ile Ile Ala Arg Tyr Ile Arg Leu His
1850                1855                1860

Pro Thr His Tyr Ser Ile Arg Ser Thr Leu Arg Met Glu Leu Met
1865                1870                1875

Gly Cys Asp Leu Asn Ser Cys Ser Met Pro Leu Gly Met Glu Ser
1880                1885                1890

Lys Ala Ile Ser Asp Ala Gln Ile Thr Ala Ser Ser Tyr Phe Thr
1895                1900                1905

Asn Met Phe Ala Thr Trp Ser Pro Ser Lys Ala Arg Leu His Leu
1910                1915                1920

Gln Gly Arg Ser Asn Ala Trp Arg Pro Gln Val Asn Asn Pro Lys
1925                1930                1935

Glu Trp Leu Gln Val Asp Phe Gln Lys Thr Met Lys Val Thr Gly
1940                1945                1950

Val Thr Thr Gln Gly Val Lys Ser Leu Leu Thr Ser Met Tyr Val
1955                1960                1965

Lys Glu Phe Leu Ile Ser Ser Gln Asp Gly His Gln Trp Thr
1970                1975                1980

Leu Phe Phe Gln Asn Gly Lys Val Lys Val Phe Gln Gly Asn Gln
1985                1990                1995

Asp Ser Phe Thr Pro Val Val Asn Ser Leu Asp Pro Pro Leu Leu
2000                2005                2010

Thr Arg Tyr Leu Arg Ile His Pro Gln Ser Trp Val His Gln Ile
2015                2020                2025

Ala Leu Arg Met Glu Val Leu Gly Cys Glu Ala Gln Asp Leu Tyr
2030                2035                2040

<210> SEQ ID NO 5
<211> LENGTH: 21
<212> TYPE: DNA

```
<213> ORGANISM: Artificial
<220> FEATURE:
<223> OTHER INFORMATION: Primer

<400> SEQUENCE: 5
cagcttgagg atccagagtt c                                          21

<210> SEQ ID NO 6
<211> LENGTH: 30
<212> TYPE: DNA
<213> ORGANISM: Artificial
<220> FEATURE:
<223> OTHER INFORMATION: Primer

<400> SEQUENCE: 6
gtgaccggtc ttttgcctag tgctagggtg                                 30

<210> SEQ ID NO 7
<211> LENGTH: 26
<212> TYPE: DNA
<213> ORGANISM: Artificial
<220> FEATURE:
<223> OTHER INFORMATION: Primer

<400> SEQUENCE: 7
gtgaccggta ggactgaaag gctgtg                                     26

<210> SEQ ID NO 8
<211> LENGTH: 23
<212> TYPE: DNA
<213> ORGANISM: Artificial
<220> FEATURE:
<223> OTHER INFORMATION: Primer

<400> SEQUENCE: 8
gattgatccg gaataatgaa gtc                                        23

<210> SEQ ID NO 9
<211> LENGTH: 34
<212> TYPE: DNA
<213> ORGANISM: Artificial
<220> FEATURE:
<223> OTHER INFORMATION: Primer

<400> SEQUENCE: 9
gcgaaccggt caggatgcac acaagagtga ggtt                            34

<210> SEQ ID NO 10
<211> LENGTH: 30
<212> TYPE: DNA
<213> ORGANISM: Artificial
<220> FEATURE:
<223> OTHER INFORMATION: Primer

<400> SEQUENCE: 10
cgcaccggtt aagcctaagg cagcttgact                                 30

<210> SEQ ID NO 11
<211> LENGTH: 29
<212> TYPE: DNA
<213> ORGANISM: Artificial
<220> FEATURE:
<223> OTHER INFORMATION: Primer

<400> SEQUENCE: 11
ctagcactag gcaaaagcag gatgcacac                                  29
```

```
<210> SEQ ID NO 12
<211> LENGTH: 29
<212> TYPE: DNA
<213> ORGANISM: Artificial
<220> FEATURE:
<223> OTHER INFORMATION: Primer

<400> SEQUENCE: 12
gtgtgcatcc tgcttttgcc tagtgctag                              29

<210> SEQ ID NO 13
<211> LENGTH: 29
<212> TYPE: DNA
<213> ORGANISM: Artificial
<220> FEATURE:
<223> OTHER INFORMATION: Primer

<400> SEQUENCE: 13
ctgccttagg cttaggtagg actgaaagg                              29

<210> SEQ ID NO 14
<211> LENGTH: 29
<212> TYPE: DNA
<213> ORGANISM: Artificial
<220> FEATURE:
<223> OTHER INFORMATION: Primer

<400> SEQUENCE: 14
cctttcagtc ctacctaagc ctaaggcag                              29

<210> SEQ ID NO 15
<211> LENGTH: 33
<212> TYPE: DNA
<213> ORGANISM: Artificial
<220> FEATURE:
<223> OTHER INFORMATION: Primer

<400> SEQUENCE: 15
ggactgaaag gctgtcctct caaaacccac cag                         33

<210> SEQ ID NO 16
<211> LENGTH: 33
<212> TYPE: DNA
<213> ORGANISM: Artificial
<220> FEATURE:
<223> OTHER INFORMATION: Primer

<400> SEQUENCE: 16
ctggtgggtt ttgagaggac agcctttcag tcc                         33

<210> SEQ ID NO 17
<211> LENGTH: 36
<212> TYPE: DNA
<213> ORGANISM: Artificial
<220> FEATURE:
<223> OTHER INFORMATION: Primer

<400> SEQUENCE: 17
caatgccatt gaaccaagct tctcccagaa ttcaag                      36

<210> SEQ ID NO 18
<211> LENGTH: 36
<212> TYPE: DNA
<213> ORGANISM: Artificial
<220> FEATURE:
<223> OTHER INFORMATION: Primer
```

-continued

```
<400> SEQUENCE: 18
cttgaattct gggagaagct tggttcaatg gcattg                                36

<210> SEQ ID NO 19
<211> LENGTH: 1671
<212> TYPE: PRT
<213> ORGANISM: Artificial
<220> FEATURE:
<223> OTHER INFORMATION: FVIII with human albumin replacing part of the
      B-domain

<400> SEQUENCE: 19

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350
```

```
Ser Glu Met Asp Val Val Arg Phe Asp Asp Asn Ser Pro Ser Phe
        355                 360                 365
Ile Gln Ile Arg Ser Val Ala Lys Lys His Pro Lys Thr Trp Val His
370                 375                 380
Tyr Ile Ala Ala Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Val Arg Phe Met Ala Tyr Thr
                420                 425                 430
Asp Glu Thr Phe Lys Thr Arg Glu Ala Ile Gln His Glu Ser Gly Ile
        435                 440                 445
Leu Gly Pro Leu Leu Tyr Gly Glu Val Gly Asp Thr Leu Leu Ile Ile
        450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
                500                 505                 510
Trp Thr Val Thr Val Glu Asp Gly Pro Thr Lys Ser Asp Pro Arg Cys
        515                 520                 525
Leu Thr Arg Tyr Tyr Ser Ser Phe Val Asn Met Glu Arg Asp Leu Ala
        530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
                580                 585                 590
Arg Phe Leu Pro Asn Pro Ala Gly Val Gln Leu Glu Asp Pro Glu Phe
                595                 600                 605
Gln Ala Ser Asn Ile Met His Ser Ile Asn Gly Tyr Val Phe Asp Ser
        610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
                660                 665                 670
Phe Ser Gly Glu Thr Val Phe Met Ser Met Glu Asn Pro Gly Leu Trp
        675                 680                 685
Ile Leu Gly Cys His Asn Ser Asp Phe Arg Asn Arg Gly Met Thr Ala
        690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Ser Phe Ser Gln Asn Ser Arg His Pro Ser Thr Arg Gln
                740                 745                 750
Lys Gln Lys Thr His Thr Cys Pro Pro Cys Pro Ala Pro Glu Leu Leu
        755                 760                 765
Gly Gly Pro Ser Val Phe Leu Phe Pro Pro Lys Pro Lys Asp Thr Leu
```

-continued

```
            770                 775                 780
Met Ile Ser Arg Thr Pro Glu Val Thr Cys Val Val Asp Val Ser
785                 790                 795                 800

His Glu Asp Pro Glu Val Lys Phe Asn Trp Tyr Val Asp Gly Val Glu
                805                 810                 815

Val His Asn Ala Lys Thr Lys Pro Arg Glu Glu Gln Tyr Asn Ser Thr
            820                 825                 830

Tyr Arg Val Val Ser Val Leu Thr Val Leu His Gln Asp Trp Leu Asn
                835                 840                 845

Gly Lys Glu Tyr Lys Cys Lys Val Ser Asn Lys Ala Leu Pro Ala Pro
850                 855                 860

Ile Glu Lys Thr Ile Ser Lys Ala Lys Gly Gln Pro Arg Glu Pro Gln
865                 870                 875                 880

Val Tyr Thr Leu Pro Pro Ser Arg Glu Glu Val Thr Lys Asn Gln Val
                885                 890                 895

Ser Leu Thr Cys Leu Val Lys Gly Phe Tyr Pro Ser Asp Ile Ala Val
                900                 905                 910

Glu Trp Glu Ser Asn Gly Gln Pro Glu Asn Asn Tyr Lys Thr Thr Pro
                915                 920                 925

Pro Val Leu Asp Ser Asp Gly Ser Phe Phe Leu Tyr Ser Lys Leu Thr
930                 935                 940

Val Asp Lys Ser Arg Trp Gln Gln Gly Asn Val Phe Ser Cys Ser Val
945                 950                 955                 960

Met His Glu Ala Leu His Asn His Tyr Thr Gln Lys Ser Leu Ser Ser
                965                 970                 975

Gln Asn Pro Pro Val Leu Lys Arg His Gln Arg Glu Ile Thr Arg Thr
                980                 985                 990

Thr Leu Gln Ser Asp Gln Glu Glu Ile Asp Tyr Asp Asp Thr Ile Ser
            995                1000                1005

Val Glu Met Lys Lys Glu Asp Phe Asp Ile Tyr Asp Glu Asp Glu
           1010                1015                1020

Asn Gln Ser Pro Arg Ser Phe Gln Lys Lys Thr Arg His Tyr Phe
           1025                1030                1035

Ile Ala Ala Val Glu Arg Leu Trp Asp Tyr Gly Met Ser Ser Ser
           1040                1045                1050

Pro His Val Leu Arg Asn Arg Ala Gln Ser Gly Ser Val Pro Gln
           1055                1060                1065

Phe Lys Lys Val Val Phe Gln Glu Phe Thr Asp Gly Ser Phe Thr
           1070                1075                1080

Gln Pro Leu Tyr Arg Gly Glu Leu Asn Glu His Leu Gly Leu Leu
           1085                1090                1095

Gly Pro Tyr Ile Arg Ala Glu Val Glu Asp Asn Ile Met Val Thr
           1100                1105                1110

Phe Arg Asn Gln Ala Ser Arg Pro Tyr Ser Phe Tyr Ser Ser Leu
           1115                1120                1125

Ile Ser Tyr Glu Glu Asp Gln Arg Gln Gly Ala Glu Pro Arg Lys
           1130                1135                1140

Asn Phe Val Lys Pro Asn Glu Thr Lys Thr Tyr Phe Trp Lys Val
           1145                1150                1155

Gln His His Met Ala Pro Thr Lys Asp Glu Phe Asp Cys Lys Ala
           1160                1165                1170

Trp Ala Tyr Phe Ser Asp Val Asp Leu Glu Lys Asp Val His Ser
           1175                1180                1185
```

-continued

Gly Leu Ile Gly Pro Leu Leu Val Cys His Thr Asn Thr Leu Asn
1190                1195                1200

Pro Ala His Gly Arg Gln Val Thr Val Gln Glu Phe Ala Leu Phe
1205                1210                1215

Phe Thr Ile Phe Asp Glu Thr Lys Ser Trp Tyr Phe Thr Glu Asn
1220                1225                1230

Met Glu Arg Asn Cys Arg Ala Pro Cys Asn Ile Gln Met Glu Asp
1235                1240                1245

Pro Thr Phe Lys Glu Asn Tyr Arg Phe His Ala Ile Asn Gly Tyr
1250                1255                1260

Ile Met Asp Thr Leu Pro Gly Leu Val Met Ala Gln Asp Gln Arg
1265                1270                1275

Ile Arg Trp Tyr Leu Leu Ser Met Gly Ser Asn Glu Asn Ile His
1280                1285                1290

Ser Ile His Phe Ser Gly His Val Phe Thr Val Arg Lys Lys Glu
1295                1300                1305

Glu Tyr Lys Met Ala Leu Tyr Asn Leu Tyr Pro Gly Val Phe Glu
1310                1315                1320

Thr Val Glu Met Leu Pro Ser Lys Ala Gly Ile Trp Arg Val Glu
1325                1330                1335

Cys Leu Ile Gly Glu His Leu His Ala Gly Met Ser Thr Leu Phe
1340                1345                1350

Leu Val Tyr Ser Asn Lys Cys Gln Thr Pro Leu Gly Met Ala Ser
1355                1360                1365

Gly His Ile Arg Asp Phe Gln Ile Thr Ala Ser Gly Gln Tyr Gly
1370                1375                1380

Gln Trp Ala Pro Lys Leu Ala Arg Leu His Tyr Ser Gly Ser Ile
1385                1390                1395

Asn Ala Trp Ser Thr Lys Glu Pro Phe Ser Trp Ile Lys Val Asp
1400                1405                1410

Leu Leu Ala Pro Met Ile Ile His Gly Ile Lys Thr Gln Gly Ala
1415                1420                1425

Arg Gln Lys Phe Ser Ser Leu Tyr Ile Ser Gln Phe Ile Ile Met
1430                1435                1440

Tyr Ser Leu Asp Gly Lys Lys Trp Gln Thr Tyr Arg Gly Asn Ser
1445                1450                1455

Thr Gly Thr Leu Met Val Phe Phe Gly Asn Val Asp Ser Ser Gly
1460                1465                1470

Ile Lys His Asn Ile Phe Asn Pro Pro Ile Ile Ala Arg Tyr Ile
1475                1480                1485

Arg Leu His Pro Thr His Tyr Ser Ile Arg Ser Thr Leu Arg Met
1490                1495                1500

Glu Leu Met Gly Cys Asp Leu Asn Ser Cys Ser Met Pro Leu Gly
1505                1510                1515

Met Glu Ser Lys Ala Ile Ser Asp Ala Gln Ile Thr Ala Ser Ser
1520                1525                1530

Tyr Phe Thr Asn Met Phe Ala Thr Trp Ser Pro Ser Lys Ala Arg
1535                1540                1545

Leu His Leu Gln Gly Arg Ser Asn Ala Trp Arg Pro Gln Val Asn
1550                1555                1560

Asn Pro Lys Glu Trp Leu Gln Val Asp Phe Gln Lys Thr Met Lys
1565                1570                1575

Val Thr Gly Val Thr Thr Gln Gly Val Lys Ser Leu Leu Thr Ser
1580                1585                1590

```
Met Tyr Val Lys Glu Phe Leu Ile Ser Ser Ser Gln Asp Gly His
    1595                1600                1605

Gln Trp Thr Leu Phe Phe Gln Asn Gly Lys Val Lys Val Phe Gln
    1610                1615                1620

Gly Asn Gln Asp Ser Phe Thr Pro Val Val Asn Ser Leu Asp Pro
    1625                1630                1635

Pro Leu Leu Thr Arg Tyr Leu Arg Ile His Pro Gln Ser Trp Val
    1640                1645                1650

His Gln Ile Ala Leu Arg Met Glu Val Leu Gly Cys Glu Ala Gln
    1655                1660                1665

Asp Leu Tyr
    1670

<210> SEQ ID NO 20
<211> LENGTH: 240
<212> TYPE: PRT
<213> ORGANISM: Artificial
<220> FEATURE:
<223> OTHER INFORMATION: Amino acid sequence of a human immunoglobulin
      G heavy chain region (240 amino acids: 1-19 human IgG signal
      peptide, 20-35 human IgG hinge region and 36-240 human IgG heavy
      chain)

<400> SEQUENCE: 20

Met Glu Phe Gly Leu Ser Trp Leu Phe Leu Val Ala Ile Leu Lys Gly
1               5                   10                  15

Val Gln Cys Lys Thr His Thr Cys Pro Pro Cys Pro Ala Pro Glu Leu
            20                  25                  30

Leu Gly Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Lys Phe Asn Trp Tyr Val Asp Gly Val
65                  70                  75                  80

Glu Val His Asn Ala Lys Thr Lys Pro Arg Glu Glu Gln Tyr Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Ala Leu Pro Ala
        115                 120                 125

Pro Ile Glu Lys Thr Ile Ser Lys Ala Lys Gly Gln Pro Arg Glu Pro
    130                 135                 140

Gln Val Tyr Thr Leu Pro Pro Ser Arg Glu Glu Val Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
    210                 215                 220

Val Met His Glu Ala Leu His Asn His Tyr Thr Gln Lys Ser Leu Ser
225                 230                 235                 240

<210> SEQ ID NO 21
<211> LENGTH: 975
```

```
<212> TYPE: PRT
<213> ORGANISM: Artificial
<220> FEATURE:
<223> OTHER INFORMATION: mature human FVIII heavy chain with partial B
      domain replacement by human immunoglobulin G heavy chain region

<400> SEQUENCE: 21
```

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

```
Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
            405                 410                 415

Gln Arg Ile Gly Arg Lys Tyr Lys Lys Val Arg Phe Met Ala Tyr Thr
        420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
        450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
            485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
            565                 570                 575

Ser Val Phe Asp Glu Asn Arg Ser Trp Tyr Leu Thr Glu Asn Ile Gln
        580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
        610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
            645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
            725                 730                 735

Ile Glu Pro Ser Phe Ser Gln Asn Ser Arg His Pro Ser Thr Arg Gln
            740                 745                 750

Lys Gln Lys Thr His Thr Cys Pro Pro Cys Pro Ala Pro Glu Leu Leu
        755                 760                 765

Gly Gly Pro Ser Val Phe Leu Phe Pro Pro Lys Pro Lys Asp Thr Leu
770                 775                 780

Met Ile Ser Arg Thr Pro Glu Val Thr Cys Val Val Val Asp Val Ser
785                 790                 795                 800

His Glu Asp Pro Glu Val Lys Phe Asn Trp Tyr Val Asp Gly Val Glu
            805                 810                 815
```

Val His Asn Ala Lys Thr Lys Pro Arg Glu Glu Gln Tyr Asn Ser Thr
820                 825                 830

Tyr Arg Val Val Ser Val Leu Thr Val Leu His Gln Asp Trp Leu Asn
            835                 840                 845

Gly Lys Glu Tyr Lys Cys Lys Val Ser Asn Lys Ala Leu Pro Ala Pro
850                 855                 860

Ile Glu Lys Thr Ile Ser Lys Ala Lys Gly Gln Pro Arg Glu Pro Gln
865                 870                 875                 880

Val Tyr Thr Leu Pro Pro Ser Arg Glu Glu Val Thr Lys Asn Gln Val
            885                 890                 895

Ser Leu Thr Cys Leu Val Lys Gly Phe Tyr Pro Ser Asp Ile Ala Val
900                 905                 910

Glu Trp Glu Ser Asn Gly Gln Pro Glu Asn Asn Tyr Lys Thr Thr Pro
            915                 920                 925

Pro Val Leu Asp Ser Asp Gly Ser Phe Phe Leu Tyr Ser Lys Leu Thr
930                 935                 940

Val Asp Lys Ser Arg Trp Gln Gln Gly Asn Val Phe Ser Cys Ser Val
945                 950                 955                 960

Met His Glu Ala Leu His Asn His Tyr Thr Gln Lys Ser Leu Ser
            965                 970                 975

<210> SEQ ID NO 22
<211> LENGTH: 917
<212> TYPE: PRT
<213> ORGANISM: Artificial
<220> FEATURE:
<223> OTHER INFORMATION: mature human FVIII light chain attached to
      human immunoglobulin G heavy chain region

<400> SEQUENCE: 22

Lys Thr His Thr Cys Pro Pro Cys Pro Ala Pro Glu Leu Leu Gly Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser His Glu
        35                  40                  45

Asp Pro Glu Val Lys Phe Asn Trp Tyr Val Asp Gly Val Glu Val His
50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
        115                 120                 125

Thr Leu Pro Pro Ser Arg Glu Glu Val Thr Lys Asn Gln Val Ser Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

```
Glu Ala Leu His Asn His Tyr Thr Gln Lys Ser Leu Ser Ser Gln Asn
    210                 215                 220

Pro Pro Val Leu Lys Arg His Gln Arg Glu Ile Thr Arg Thr Thr Leu
225                 230                 235                 240

Gln Ser Asp Gln Glu Glu Ile Asp Tyr Asp Thr Ile Ser Val Glu
                245                 250                 255

Met Lys Lys Glu Asp Phe Asp Ile Tyr Asp Glu Asp Asn Gln Ser
                260                 265                 270

Pro Arg Ser Phe Gln Lys Lys Thr Arg His Tyr Phe Ile Ala Ala Val
                275                 280                 285

Glu Arg Leu Trp Asp Tyr Gly Met Ser Ser Pro His Val Leu Arg
    290                 295                 300

Asn Arg Ala Gln Ser Gly Ser Val Pro Gln Phe Lys Lys Val Val Phe
305                 310                 315                 320

Gln Glu Phe Thr Asp Gly Ser Phe Thr Gln Pro Leu Tyr Arg Gly Glu
                325                 330                 335

Leu Asn Glu His Leu Gly Leu Leu Gly Pro Tyr Ile Arg Ala Glu Val
                340                 345                 350

Glu Asp Asn Ile Met Val Thr Phe Arg Asn Gln Ala Ser Arg Pro Tyr
                355                 360                 365

Ser Phe Tyr Ser Ser Leu Ile Ser Tyr Glu Glu Asp Gln Arg Gln Gly
    370                 375                 380

Ala Glu Pro Arg Lys Asn Phe Val Lys Pro Asn Glu Thr Lys Thr Tyr
385                 390                 395                 400

Phe Trp Lys Val Gln His His Met Ala Pro Thr Lys Asp Glu Phe Asp
                405                 410                 415

Cys Lys Ala Trp Ala Tyr Phe Ser Asp Val Asp Leu Glu Lys Asp Val
                420                 425                 430

His Ser Gly Leu Ile Gly Pro Leu Leu Val Cys His Thr Asn Thr Leu
    435                 440                 445

Asn Pro Ala His Gly Arg Gln Val Thr Val Gln Glu Phe Ala Leu Phe
450                 455                 460

Phe Thr Ile Phe Asp Glu Thr Lys Ser Trp Tyr Phe Thr Glu Asn Met
465                 470                 475                 480

Glu Arg Asn Cys Arg Ala Pro Cys Asn Ile Gln Met Glu Asp Pro Thr
                485                 490                 495

Phe Lys Glu Asn Tyr Arg Phe His Ala Ile Asn Gly Tyr Ile Met Asp
                500                 505                 510

Thr Leu Pro Gly Leu Val Met Ala Gln Asp Gln Arg Ile Arg Trp Tyr
    515                 520                 525

Leu Leu Ser Met Gly Ser Asn Glu Asn Ile His Ser Ile His Phe Ser
    530                 535                 540

Gly His Val Phe Thr Val Arg Lys Lys Glu Glu Tyr Lys Met Ala Leu
545                 550                 555                 560

Tyr Asn Leu Tyr Pro Gly Val Phe Glu Thr Val Glu Met Leu Pro Ser
                565                 570                 575

Lys Ala Gly Ile Trp Arg Val Glu Cys Leu Ile Gly Glu His Leu His
                580                 585                 590

Ala Gly Met Ser Thr Leu Phe Leu Val Tyr Ser Asn Lys Cys Gln Thr
    595                 600                 605

Pro Leu Gly Met Ala Ser Gly His Ile Arg Asp Phe Gln Ile Thr Ala
610                 615                 620

Ser Gly Gln Tyr Gly Gln Trp Ala Pro Lys Leu Ala Arg Leu His Tyr
```

```
                625                 630                 635                 640
Ser Gly Ser Ile Asn Ala Trp Ser Thr Lys Glu Pro Phe Ser Trp Ile
                    645                 650                 655

Lys Val Asp Leu Leu Ala Pro Met Ile Ile His Gly Ile Lys Thr Gln
                660                 665                 670

Gly Ala Arg Gln Lys Phe Ser Ser Leu Tyr Ile Ser Gln Phe Ile Ile
                675                 680                 685

Met Tyr Ser Leu Asp Gly Lys Lys Trp Gln Thr Tyr Arg Gly Asn Ser
            690                 695                 700

Thr Gly Thr Leu Met Val Phe Phe Gly Asn Val Asp Ser Ser Gly Ile
705                 710                 715                 720

Lys His Asn Ile Phe Asn Pro Pro Ile Ile Ala Arg Tyr Ile Arg Leu
                725                 730                 735

His Pro Thr His Tyr Ser Ile Arg Ser Thr Leu Arg Met Glu Leu Met
                740                 745                 750

Gly Cys Asp Leu Asn Ser Cys Ser Met Pro Leu Gly Met Glu Ser Lys
            755                 760                 765

Ala Ile Ser Asp Ala Gln Ile Thr Ala Ser Ser Tyr Phe Thr Asn Met
770                 775                 780

Phe Ala Thr Trp Ser Pro Ser Lys Ala Arg Leu His Leu Gln Gly Arg
785                 790                 795                 800

Ser Asn Ala Trp Arg Pro Gln Val Asn Asn Pro Lys Glu Trp Leu Gln
                805                 810                 815

Val Asp Phe Gln Lys Thr Met Lys Val Thr Gly Val Thr Thr Gln Gly
            820                 825                 830

Val Lys Ser Leu Leu Thr Ser Met Tyr Val Lys Glu Phe Leu Ile Ser
            835                 840                 845

Ser Ser Gln Asp Gly His Gln Trp Thr Leu Phe Phe Gln Asn Gly Lys
        850                 855                 860

Val Lys Val Phe Gln Gly Asn Gln Asp Ser Phe Thr Pro Val Val Asn
865                 870                 875                 880

Ser Leu Asp Pro Pro Leu Leu Thr Arg Tyr Leu Arg Ile His Pro Gln
                885                 890                 895

Ser Trp Val His Gln Ile Ala Leu Arg Met Glu Val Leu Gly Cys Glu
                900                 905                 910

Ala Gln Asp Leu Tyr
        915

<210> SEQ ID NO 23
<211> LENGTH: 31
<212> TYPE: PRT
<213> ORGANISM: Artificial
<220> FEATURE:
<223> OTHER INFORMATION: Linker

<400> SEQUENCE: 23

Asn Asn Ala Ile Glu Pro Ser Phe Ser Gln Asn Ser Arg His Pro Ser
1               5                   10                  15

Thr Arg Gln Lys Gln Asp Ala His Lys Ser Glu Val Ala His Arg
            20                  25                  30

<210> SEQ ID NO 24
<211> LENGTH: 32
<212> TYPE: PRT
<213> ORGANISM: Artificial
<220> FEATURE:
<223> OTHER INFORMATION: Linker
```

<400> SEQUENCE: 24

Asn Asn Ala Ile Glu Pro Arg Ser Phe Ser Gln Asn Ser Arg His Pro
1               5                   10                  15

Ser Thr Arg Gln Lys Gln Asp Ala His Lys Ser Glu Val Ala His Arg
            20                  25                  30

<210> SEQ ID NO 25
<211> LENGTH: 30
<212> TYPE: PRT
<213> ORGANISM: Artificial
<220> FEATURE:
<223> OTHER INFORMATION: Linker

<400> SEQUENCE: 25

Asn Asn Ala Ile Glu Pro Arg Ser Phe Ser Gln Asn Ser Arg His Pro
1               5                   10                  15

Ser Thr Arg Gln Asp Ala His Lys Ser Glu Val Ala His Arg
            20                  25                  30

<210> SEQ ID NO 26
<211> LENGTH: 28
<212> TYPE: PRT
<213> ORGANISM: Artificial
<220> FEATURE:
<223> OTHER INFORMATION: Linker

<400> SEQUENCE: 26

Asn Asn Ala Ile Glu Pro Arg Ser Phe Ser Gln Asn Ser Arg His Pro
1               5                   10                  15

Ser Thr Asp Ala His Lys Ser Glu Val Ala His Arg
            20                  25

<210> SEQ ID NO 27
<211> LENGTH: 25
<212> TYPE: PRT
<213> ORGANISM: Artificial
<220> FEATURE:
<223> OTHER INFORMATION: Linker

<400> SEQUENCE: 27

Asn Asn Ala Ile Glu Pro Arg Ser Phe Ser Gln Asn Ser Arg His Asp
1               5                   10                  15

Ala His Lys Ser Glu Val Ala His Arg
            20                  25

<210> SEQ ID NO 28
<211> LENGTH: 23
<212> TYPE: PRT
<213> ORGANISM: Artificial
<220> FEATURE:
<223> OTHER INFORMATION: Linker

<400> SEQUENCE: 28

Asn Asn Ala Ile Glu Pro Arg Ser Phe Ser Gln Asn Ser Asp Ala His
1               5                   10                  15

Lys Ser Glu Val Ala His Arg
            20

<210> SEQ ID NO 29
<211> LENGTH: 20
<212> TYPE: PRT
<213> ORGANISM: Artificial
<220> FEATURE:
<223> OTHER INFORMATION: Linker

```
<400> SEQUENCE: 29

Asn Asn Ala Ile Glu Pro Arg Ser Phe Ser Asp Ala His Lys Ser Glu
1               5                   10                  15

Val Ala His Arg
            20

<210> SEQ ID NO 30
<211> LENGTH: 32
<212> TYPE: PRT
<213> ORGANISM: Artificial
<220> FEATURE:
<223> OTHER INFORMATION: Linker

<400> SEQUENCE: 30

Asn Asn Ala Ile Glu Pro Arg Ser Phe Ser Gln Asn Ser Gly Gly Ser
1               5                   10                  15

Gly Gly Ser Gly Gly Ser Asp Ala His Lys Ser Glu Val Ala His Arg
            20                  25                  30

<210> SEQ ID NO 31
<211> LENGTH: 27
<212> TYPE: PRT
<213> ORGANISM: Artificial
<220> FEATURE:
<223> OTHER INFORMATION: Linker

<400> SEQUENCE: 31

Asn Asn Ala Ile Glu Pro Arg Ser Val Ala Lys Lys His Pro Lys Thr
1               5                   10                  15

Trp Asp Ala His Lys Ser Glu Val Ala His Arg
            20                  25

<210> SEQ ID NO 32
<211> LENGTH: 27
<212> TYPE: PRT
<213> ORGANISM: Artificial
<220> FEATURE:
<223> OTHER INFORMATION: Linker

<400> SEQUENCE: 32

Asn Asn Ala Ile Glu Pro Arg Ser Phe Gln Lys Lys Thr Arg His Tyr
1               5                   10                  15

Phe Asp Ala His Lys Ser Glu Val Ala His Arg
            20                  25

<210> SEQ ID NO 33
<211> LENGTH: 21
<212> TYPE: PRT
<213> ORGANISM: Artificial
<220> FEATURE:
<223> OTHER INFORMATION: Linker

<400> SEQUENCE: 33

Asn Asn Ala Ile Glu Pro Arg Ala Val Gly Gly Asp Ala His Lys Ser
1               5                   10                  15

Glu Val Ala His Arg
            20

<210> SEQ ID NO 34
<211> LENGTH: 36
<212> TYPE: PRT
<213> ORGANISM: Artificial
<220> FEATURE:
<223> OTHER INFORMATION: Linker
```

```
<400> SEQUENCE: 34

Val Ala Ala Ser Gln Ala Ala Leu Gly Leu Gly Arg Thr Glu Arg Leu
1               5                   10                  15

Cys Ser Gln Asn Pro Pro Val Leu Lys Arg His Gln Arg Glu Ile Thr
            20                  25                  30

Arg Thr Thr Leu
        35

<210> SEQ ID NO 35
<211> LENGTH: 36
<212> TYPE: PRT
<213> ORGANISM: Artificial
<220> FEATURE:
<223> OTHER INFORMATION: Linker

<400> SEQUENCE: 35

Val Ala Ala Ser Gln Ala Ala Leu Gly Leu Gly Arg Thr Glu Arg Leu
1               5                   10                  15

Ser Ser Gln Asn Pro Pro Val Leu Lys Arg His Gln Arg Glu Ile Thr
            20                  25                  30

Arg Thr Thr Leu
        35

<210> SEQ ID NO 36
<211> LENGTH: 34
<212> TYPE: PRT
<213> ORGANISM: Artificial
<220> FEATURE:
<223> OTHER INFORMATION: Linker

<400> SEQUENCE: 36

Val Ala Ala Ser Gln Ala Ala Leu Gly Leu Thr Glu Arg Leu Cys Ser
1               5                   10                  15

Gln Asn Pro Pro Val Leu Lys Arg His Gln Arg Glu Ile Thr Arg Thr
            20                  25                  30

Thr Leu

<210> SEQ ID NO 37
<211> LENGTH: 34
<212> TYPE: PRT
<213> ORGANISM: Artificial
<220> FEATURE:
<223> OTHER INFORMATION: Linker

<400> SEQUENCE: 37

Val Ala Ala Ser Gln Ala Ala Leu Gly Leu Thr Glu Arg Leu Ser Ser
1               5                   10                  15

Gln Asn Pro Pro Val Leu Lys Arg His Gln Arg Glu Ile Thr Arg Thr
            20                  25                  30

Thr Leu

<210> SEQ ID NO 38
<211> LENGTH: 31
<212> TYPE: PRT
<213> ORGANISM: Artificial
<220> FEATURE:
<223> OTHER INFORMATION: Linker

<400> SEQUENCE: 38

Val Ala Ala Ser Gln Ala Ala Leu Gly Leu Leu Cys Ser Gln Asn Pro
1               5                   10                  15

Pro Val Leu Lys Arg His Gln Arg Glu Ile Thr Arg Thr Thr Leu
```

-continued

```
              20                  25                  30

<210> SEQ ID NO 39
<211> LENGTH: 31
<212> TYPE: PRT
<213> ORGANISM: Artificial
<220> FEATURE:
<223> OTHER INFORMATION: Linker

<400> SEQUENCE: 39

Val Ala Ala Ser Gln Ala Ala Leu Gly Leu Leu Ser Ser Gln Asn Pro
1               5                  10                  15

Pro Val Leu Lys Arg His Gln Arg Glu Ile Thr Arg Thr Thr Leu
            20                  25                  30

<210> SEQ ID NO 40
<211> LENGTH: 29
<212> TYPE: PRT
<213> ORGANISM: Artificial
<220> FEATURE:
<223> OTHER INFORMATION: Linker

<400> SEQUENCE: 40

Val Ala Ala Ser Gln Ala Ala Leu Gly Leu Ser Gln Asn Pro Pro Val
1               5                  10                  15

Leu Lys Arg His Gln Arg Glu Ile Thr Arg Thr Thr Leu
            20                  25

<210> SEQ ID NO 41
<211> LENGTH: 24
<212> TYPE: PRT
<213> ORGANISM: Artificial
<220> FEATURE:
<223> OTHER INFORMATION: Linker

<400> SEQUENCE: 41

Val Ala Ala Ser Gln Ala Ala Leu Gly Leu Val Leu Lys Arg His Gln
1               5                  10                  15

Arg Glu Ile Thr Arg Thr Thr Leu
            20

<210> SEQ ID NO 42
<211> LENGTH: 21
<212> TYPE: PRT
<213> ORGANISM: Artificial
<220> FEATURE:
<223> OTHER INFORMATION: Linker

<400> SEQUENCE: 42

Val Ala Ala Ser Gln Ala Ala Leu Gly Leu Arg His Gln Arg Glu Ile
1               5                  10                  15

Thr Arg Thr Thr Leu
            20

<210> SEQ ID NO 43
<211> LENGTH: 36
<212> TYPE: PRT
<213> ORGANISM: Artificial
<220> FEATURE:
<223> OTHER INFORMATION: Linker

<400> SEQUENCE: 43

Val Ala Ala Ser Gln Ala Ala Leu Gly Leu Gly Arg Thr Glu Arg Leu
1               5                  10                  15

Cys Ser Gln Asn Pro Pro Val Leu Lys Arg His Arg Arg Glu Ile Thr
```

```
                    20                  25                  30

Arg Thr Thr Leu
        35

<210> SEQ ID NO 44
<211> LENGTH: 29
<212> TYPE: PRT
<213> ORGANISM: Artificial
<220> FEATURE:
<223> OTHER INFORMATION: Linker

<400> SEQUENCE: 44

Val Ala Ala Ser Gln Ala Ala Leu Gly Leu Ser Gln Asn Pro Pro Val
1               5                   10                  15

Leu Lys Arg His Arg Arg Glu Ile Thr Arg Thr Thr Leu
                20                  25

<210> SEQ ID NO 45
<211> LENGTH: 21
<212> TYPE: PRT
<213> ORGANISM: Artificial
<220> FEATURE:
<223> OTHER INFORMATION: Linker

<400> SEQUENCE: 45

Val Ala Ala Ser Gln Ala Ala Leu Gly Leu Arg His Arg Arg Glu Ile
1               5                   10                  15

Thr Arg Thr Thr Leu
                20

<210> SEQ ID NO 46
<211> LENGTH: 36
<212> TYPE: PRT
<213> ORGANISM: Artificial
<220> FEATURE:
<223> OTHER INFORMATION: Linker

<400> SEQUENCE: 46

Val Ala Ala Ser Gln Ala Ala Leu Gly Leu Gly Gly Ser Gly Gly Ser
1               5                   10                  15

Gly Gly Ser Gly Gly Ser Gly Gly Ser Arg His Arg Arg Glu Ile Thr
                20                  25                  30

Arg Thr Thr Leu
        35

<210> SEQ ID NO 47
<211> LENGTH: 33
<212> TYPE: PRT
<213> ORGANISM: Artificial
<220> FEATURE:
<223> OTHER INFORMATION: Linker

<400> SEQUENCE: 47

Val Ala Ala Ser Gln Ala Ala Leu Gly Leu Gly Gly Ser Gly Gly Ser
1               5                   10                  15

Gly Gly Ser Gly Gly Ser Arg His Arg Arg Glu Ile Thr Arg Thr Thr
                20                  25                  30

Leu

<210> SEQ ID NO 48
<211> LENGTH: 27
<212> TYPE: PRT
<213> ORGANISM: Artificial
<220> FEATURE:
```

```
-continued

<223> OTHER INFORMATION: Linker

<400> SEQUENCE: 48

Val Ala Ala Ser Gln Ala Ala Leu Gly Leu Gly Gly Ser Gly Gly Ser
1               5                   10                  15

Arg His Arg Arg Glu Ile Thr Arg Thr Thr Leu
            20                  25

<210> SEQ ID NO 49
<211> LENGTH: 27
<212> TYPE: PRT
<213> ORGANISM: Artificial
<220> FEATURE:
<223> OTHER INFORMATION: Linker

<400> SEQUENCE: 49

Val Ala Ala Ser Gln Ala Ala Leu Gly Leu Gly Gly Ser Gly Gly Ser
1               5                   10                  15

Arg His Arg Arg Glu Ile Thr Arg Thr Thr Leu
            20                  25
```